United States Patent
Vallejo Illarramendi et al.

(10) Patent No.: US 11,377,427 B2
(45) Date of Patent: Jul. 5, 2022

(54) TRIAZOLES FOR REGULATING INTRACELLULAR CALCIUM HOMEOSTASIS

(71) Applicants: UNIVERSIDAD DEL PAIS VASCO, Leioa-Vizcaya (ES); ADMINISTRACION GENERAL DE LA COMUNIDAD AUTONOMA DE EUSKADI, Vitoria-Gasteiz-Alava (ES)

(72) Inventors: Ainara Vallejo Illarramendi, San Sebastian-Guipuzcoa (ES); Adolfo Jose Lopez De Munain Arregi, San Sebastian-Guipuzcoa (ES); Pablo Ferron Celma, Donostia-San Sebastian (ES); Jesus Maria Aizpurua Iparraguirre, Leioa-Vizcaya (ES); Aitziber Irastorza Epelde, Leioa-Vizcaya (ES); Jose Ignacio Miranda Murua, Leioa-Vizcaya (ES); Ivan Toral Ojeda, San Sebastian-Guipuzcoa (ES); Garazi Aldanondo Aristizabal, San Sebastian-Guipuzcoa (ES)

(73) Assignees: UNIVERSIDAD DEL PAIS VASCO, Leioa-Vizcaya (ES); ADMINISTRACION GENERAL DE LA COMUNIDAD AUTONOMA DE EUSKADI, Vitoria-Gasteiz-Alava (ES)

( * ) Notice: Subject to any disclaimer, the term of this patent is extended or adjusted under 35 U.S.C. 154(b) by 447 days.

(21) Appl. No.: 16/304,041

(22) PCT Filed: May 23, 2017

(86) PCT No.: PCT/ES2017/070344
§ 371 (c)(1),
(2) Date: Nov. 21, 2018

(87) PCT Pub. No.: WO2017/203083
PCT Pub. Date: Nov. 30, 2017

(65) Prior Publication Data
US 2020/0317625 A1 Oct. 8, 2020

(30) Foreign Application Priority Data
May 24, 2016 (ES) .................................. 201630670

(51) Int. Cl.
C07D 249/04 (2006.01)
A61P 21/00 (2006.01)
A61P 9/04 (2006.01)
A61K 9/00 (2006.01)

(52) U.S. Cl.
CPC .............. *C07D 249/04* (2013.01); *A61P 9/04* (2018.01); *A61P 21/00* (2018.01); *A61K 9/0029* (2013.01); *A61K 9/0053* (2013.01)

(58) Field of Classification Search
CPC ........... C07D 249/04; A61P 21/00; A61P 9/04
See application file for complete search history.

(56) References Cited

U.S. PATENT DOCUMENTS

| 5,416,066 | A | 5/1995 | Kaneko | |
|---|---|---|---|---|
| 7,067,057 | B2 * | 6/2006 | Rosenberger | C02F 1/44 210/195.2 |
| 2004/0229781 | A1 | 11/2004 | Marks et al. | |
| 2006/0194767 | A1 | 8/2006 | Marks et al. | |
| 2007/0254849 | A1 | 11/2007 | Chen et al. | |
| 2008/0108630 | A1 | 5/2008 | Zhu et al. | |
| 2013/0137765 | A1 | 5/2013 | Clementi et al. | |

FOREIGN PATENT DOCUMENTS

| CN | 101500576 A | 8/2009 |
|---|---|---|
| EP | 2857388 A1 | 4/2015 |
| RU | 2006145872 A | 6/2008 |
| WO | 9212148 A1 | 7/1992 |
| WO | 2006044412 A1 | 4/2006 |
| WO | 2007091106 A2 | 8/2007 |
| WO | 2008060332 A2 | 5/2008 |
| WO | 2008144483 A2 | 11/2008 |
| WO | 2009019505 A2 | 2/2009 |
| WO | 2010057833 A1 | 5/2010 |
| WO | 2012019071 A1 | 2/2012 |

(Continued)

OTHER PUBLICATIONS

Zawilska. Pharmacological Reports, 2013, 65 1-14 (Year: 2013).*
Lanner. Calcium Signaling, 2012, bibliographic data and table of contents, and chapter 9, pp. 217-234 (Year: 2012).*
McGreevy. Disease Models and Mechanisms, 2015, 8, 195-213 (Year: 2015).*
Petrini. Synthesis, 2009, 18, 3143-3149 (Year: 2009).*
Vallejo-Illarramendi et al., "Dysregulation of calcium homeostasis in muscular dystrophies", expert reviews in molecular medicine, 2014, vol. 16, e16, pp. 1-23.

(Continued)

*Primary Examiner* — Noble E Jarrell
(74) *Attorney, Agent, or Firm* — Lucas & Mercanti, LLP

(57) ABSTRACT

The present invention relates to 1,2,3-triazoles of formula:

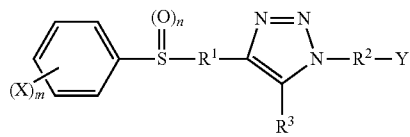

useful for improving or restoring the intracellular calcium homeostasis and RyR-calstabin binding function in human and animal cells. The present invention also relates to methods for synthesizing said compounds, to pharmaceutical compositions containing them, and to the use thereof for preventing or treating skeletal muscle, heart and nervous system disorders.

18 Claims, 8 Drawing Sheets

(56) References Cited

FOREIGN PATENT DOCUMENTS

| WO | 2012037105 A1 | 3/2012 |
|---|---|---|
| WO | 2013085890 A1 | 6/2013 |
| WO | 2013142346 A1 | 9/2013 |
| WO | 2013156505 A1 | 10/2013 |
| WO | 2014205414 A1 | 12/2014 |
| WO | 2015061685 A1 | 4/2015 |
| WO | 2015107541 A1 | 7/2015 |
| WO | 2016057656 A1 | 4/2016 |

OTHER PUBLICATIONS

Dudley et al., "Sarcolemmal Damage in Dystrophin Deficiency Is Modulated by Synergistic Interactions between Mechanical and Oxidative/Nitrosative Stresses", American Journal of Pathology, 2006, vol. 168, No. 4, pp. 1276-1284.
Bellinger et ai., "Hypernitrosylated ryanodine receptor calcium release channels are leaky in dystrophic muscle", Nature Medicine, 2009, vol. 15, No. 3, pp. 325-330.
Fauconnier et al., "Leaky RyR2 trigger ventricular arrhythmias in Duchenne muscular dystrophy", PNAS, 2010, vol. 7, No. 4, pp. 1559-1564.
Kushnir et aL., "Ryanodine Receptor Patents", Recent Pat Biotechnol, 2012, vol. 6, No. 3, pp. 157-166.
Mei et al., "Stabilization of the Skeletal Muscle Ryanodine Receptor ion Channel-FKBP12 Complex by the 1,4-Benzothiazepine Derivative S107", Plos One, 2013, vol. 8, Issue 1, pp. 1-12.
Kakizawa et al., "Nitric oxide-induced calcium release via ryanodine receptors regulates neuronal function", The EMBO Journal, 2012, vol. 31, No. 2, pp. 417-428.
Liu et ai., "Role of Leaky Neuronal Ryanodine Receptors in Stress-Induced Cognitive Dysfunction", Cell., 2012, vol. 150, No. 5, pp. 1055-1067.
Brillantes et al., "Stabilization of Calcium Release Channel (Ryanodine Receptor) Function by FK506-Binding Protein", Cell, 1994, vol. 77, pp. 513-523.
Gillo et al., "Calcium Influx in induced Differentiation of Murine Erythroleukemia Cells", Blood, 1993, vol. 81, No. 3, pp. 783-792.
Thevis et al., "Screening for the caistabin-ryanodine receptor complex stabilizers JTV-519 and S-107 in doping control analysis", Drug Testing and Analysis, 2009, vol. 1, pp. 32-42.
A. Vallejo-Illarramendi, et al.; Dysregulation of calcium homeostasis in muscular dystrophies; Expert Reviews in Molecular Medicine; vol. 16; 2014; pp. 1-23.
C. Ferroni, et al.; 1,4-Substituted triazoles as nonsteroidal antiandrogens for prostate cancer treatment; Journal of Medicinal Chemistry; vol. 60; 2017; pp. 3082-3093.
P. Joshi, et al.; Synthesis and characterization of theophyllinetriazole and theophylline-triazole-coumarin based molecular hybrids; Indian Journal of Heterocyclic Chemistry; vol. 24; 2015; pp. 411-418.
XP-002773850; Database Registry No. 2094316-11-5.
XP-002773851; Database Registry No. 2094391-58-7.
International Search Report and Written Opinion dated Oct. 25, 2017 for PCT/ES2017/070344 and English translation.
International Preliminary Report on Patentability dated May 18, 2018 for PCT/ES2017/070344 and English translation.

\* cited by examiner

TRIAZOLES FOR REGULATING INTRACELLULAR CALCIUM HOMEOSTASIS

CROSS REFERENCE TO RELATED APPLICATION

This Application is a 371 of PCT/ES2017/070344 filed on May 23, 2017 which, in turn, claimed the priority of Spanish Patent Application No. P201630670 filed on May 24, 2016, both applications are incorporated herein by reference.

FIELD OF THE INVENTION

The present invention relates to new substituted 1,2,3-triazoles useful for improving or restoring intracellular calcium homeostasis function in human and animal cells. The present invention also relates to methods for synthesizing said compounds, to pharmaceutical compositions containing them, and to the use thereof for preventing or treating skeletal muscle, heart and neurodegenerative disorders.

BACKGROUND OF THE INVENTION

Muscular dystrophies are heterogeneous hereditary diseases characterized by progressive weakening and atrophy of the skeletal muscle. X-linked Duchenne muscular dystrophy (DMD) is one of the most common forms affecting 1 out of every 3500 males. As in the case of its more benign allelic form (Becker muscular dystrophy, BMD), both DMD and BMD are caused by mutations in the gene encoding dystrophin, a 427-kDa cytoskeleton protein. Genetic studies are not enough to eradicate the disease due to the high incidence of sporadic cases, so the search for new effective therapies is therefore an urgent need.

Limb-girdle muscular dystrophies (LGMDs) are a large group of hereditary muscular dystrophies characterized by progressive proximal weakness predominantly involving the pelvic and shoulder girdles. Among the recessive forms of LGMD, calpainopathy or LGMD2A is the most common form and is caused by mutations in the gene encoding calpain 3 (CAPN3), a non-lysosomal cysteine protease necessary for correct muscle functioning and regeneration.

Myotonic dystrophy type 1 (DM1) is the most common form of muscular dystrophy in adults and is characterized by muscle weakness, myotonia and multisystemic involvement. It is a dominant autosomal hereditary disease caused by an unstable expansion of the CTG triplet repeat located in the 3' non-coding region of the DMPK gene located on the long arm of chromosome 19 and predominantly expressed in skeletal muscle.

Alterations in intracellular calcium homeostasis are shared by the aforementioned as well as other muscular dystrophies (such as DM2, recessive and dominant LGMD, congenital or metabolic myopathies, among others). Due to the fact that an alteration of the intracellular $Ca^{2+}$ concentration in muscle fibers seems to represent a common central pathogenic mechanism, the development of therapeutic interventions preventing alterations of intracellular $Ca^{2+}$ is a very valuable therapeutic target. (Vallejo-Illarramendi et al. *Expert Rev. Molec. Med.* 2014, 16, e16, doi: 10.1017/erm.2014.17 "Dysregulation of calcium homeostasis in muscular dystrophies").

High baseline intracellular $Ca^{2+}$ levels lead to the activation of calpain, degradation of proteins, opening of mitochondrial permeability transition pores (mPTPs), and finally death of the muscle fiber due to necrosis. The increase in intracellular $Ca^{2+}$ levels is a complex process involving $Ca^{2+}$ fluxes through the sarcolemma, calcium losses from the sarcoplasmic reticulum (SR) and abnormal $Ca^{2+}$ levels in the SR. In mdx mice, an animal model of Duchenne muscular dystrophy, abnormal S-nitrosylation of the cysteine residues of ryanodine receptors, RyR1 and RyR2, leads to the dissociation of calstabin from the protein complex, which produces unstable channels that lose calcium at rest. This nitrosylation seems to be brought about by a nitric oxide dysregulation that causes nitrosative and oxidative stress in the muscle of dystrophic mdx mice (Dudley et al., *Am. J. Pathol.* 2006, 168, 1276-1284; Bellinger et al., *Nat Med.* 2009, 15, 325-330; Fauconier et al., *Proc. Natl. Acad. Sci. USA.* 2010, 107, 1559-1564). Furthermore, the induced expression of microdystrophin in dystrophin-deficient microtubes reverts the increase in inositol 1,4,5-trisphosphate receptor (IP3R)-dependent calcium release back to control levels, which suggests IP3R involvement in the alteration of $Ca^{2+}$ homeostasis in DMD.

Calpain 3 (CAPN3) has been proven by means of immunoprecipitation assays to interact with calsequestrin (CSQ), a protein participating in calcium homeostasis. In CAPN3-knockout mice (C3KO, Capn3–/–), the reduction in RyR1 levels is accompanied by a reduction in $Ca^{2+}$ release from the SR. In turn, it has been found that after calcium release from the SR in Capn3–/– mice, $Ca^{2+}$ reuptake into the SR occurs more slowly, although the basis of this finding requires more in-depth studies. However, it has been observed that CAPN3 proteolytic activity loss in Capn3 cs/cs mice does not affect calcium homeostasis, which indicates that the structural function of CAPN3 is key for maintaining $Ca^{2+}$ homeostasis.

Myotonic dystrophy has been associated with the dysregulation of the alternative connection of the CACNA1S gene encoding the alpha 1S subunit of the dihydropyridine receptor DHPR, a voltage sensor that is essential in excitation-contraction (E-C) coupling. In DM1 and DM2, there is greater CACNA1S exon 29 omission, which increases channel conductance and voltage sensitivity.

Several disorders and diseases are associated with congenital or acquired RyR1 protein modifications (Kushmir et al. *Recent Pat Biotechnol.* 2012, 6, 157-166 "Ryanodine receptor patents"). Said disorders and diseases comprise skeletal muscle, heart and nervous system conditions. More specifically they include, but are not limited to, congenital myopathies, muscular dystrophies, sarcopenia, skeletal muscle fatigue, acquired muscle weakness or atrophy, malignant hyperthermia, exercise-induced cardiac arrhythmias, congestive heart failure, hypertrophic cardiomyopathy, Alzheimer's disease and age-related memory loss. It has been suggested for all these conditions that increasing intracellular $Ca^{2+}$ concentrations ($[Ca^{2+}]_i$) in resting conditions contribute directly to toxicity of the cell (myofiber, cardiomyocyte, neuron or glial cell), its deterioration and the simultaneous activation of $Ca^{2+}$-dependent proteases.

There are two main types of calcium channel-related ryanodine receptors in muscle fibers: RyR1 located in the skeletal muscle, and RyR2 located in the heart muscle. Each calcium channel is formed by an RyR protein tetramer, each RyR monomer being able to interact with a calstabin protein. RyR1 binds to FKBP12 (calstabin1) and RyR2 binds to FKBP12.6 (calstabin2). It has been found both in the heart and skeletal muscle that the abnormal dissociation of calstabins and RyR channels by progressive RyR channel nitrosylation causes an increase in $Ca^{2+}$ release from the sarcoplasmic reticulum into the intracellular cytoplasm, reducing muscle performance during contraction and activating muscle dysfunction in the long term (Bellinger et al., *Nat. Med.* 2009, 15, 325-330; Fauconier et al., *Proc. Natl. Acad. Sci. USA.* 2010, 107, 1559-1564).

Some low molecular weight compounds showing therapeutic activity in damaged muscle tissues are known in the state of the art. The usefulness of 4-[3-(4-benzylpiperidinyl)-propanoyl]-2,3,4,5-tetrahydro-1,4-benzothiazepine (JTV-519) for preventing heart muscle necrosis and myocardial infarction has been demonstrated, for example. At concentrations of $10^{-6}$ M, compound JTV-519 inhibits in vitro adrenaline- and caffeine-induced myocardial necrosis in the left ventricle of a rat heart without affecting left ventricular heart rate or pressure (Kaneko, N. et al. WO92/12148A1 "Preparation of 4-[(4-benzylpiperidinyl)-alkanoyl]-2,3,4,5-tetrahydro-1,4-benzothiazepine derivatives for inhibiting the kinetic cell death of cardiac muscles without inhibiting cardiac functions"). Compound JTV-519 acts on the calstabin2-associated RyR2 ryanodine receptor (FKBP12.6), increasing FKBP12.6 affinity for the PKA kinase-phosphorylated RyR2 receptor, and also for the mutant RyR2 receptor, which otherwise has a reduced affinity for or does not bind to FKBP12.6. This action of JTV-519 fixes the $Cat^{2+}$ ion leak in RyR2 (Marks, A. R. et al. US2004/229781A1 "Compounds and methods for treating and preventing exercise-induced cardiac arrhythmias").

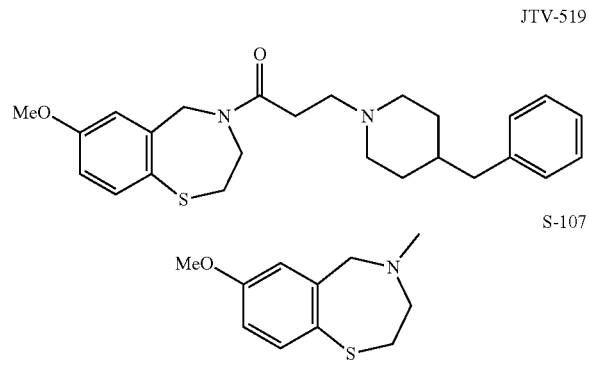

JTV-519

S-107

Pharmaceutically active compositions containing compound S-107, or other structurally related tetrahydrobenzothiazepines, are also known to be effective for treating or preventing disorders or diseases related to RyR2 receptors which regulate calcium channel functioning in cardiac cells (Marks, A. R. et al. US2006/194767A1 "Benzothiazepines as novel agents for preventing and treating disorders involving modulation of the RyR receptors and their preparation and pharmaceutical compositions"; see also: Mei, Y. et al. *PLoS One.* 2013, 8: e54208 "Stabilization of the skeletal muscle ryanodine receptor ion channel-FKBP12 complex by the 1,4-benzothiazepine derivative S107"). The same family of compounds is also known to be active as an RyR1-calstabin1 interaction stabilizer, reducing muscle fatigue (Marks, A. R. et al. WO2008/060332A2 "Methods using tetrahydrobenzothiazepine compounds for treating or reducing muscle fatigue"), and for treating sarcopenia (Marks, A. R. et al. WO2012/019071A1 "Methods and compositions comprising benzazepine derivatives for preventing and treating sarcopenia").

Some carvedilol derivatives have been described to assist in normalization of intracellular calcium homeostasis through the action on RyR2 receptors, thereby proving a beneficial effect in cardiac therapy (Chen, S. et al. US2007/025489A1 "Preparation of carbazoles as ryanodine receptor type 2 (RyR2) antagonists for treatment of cardiac conditions").

Finally, the ryanodine RyR3 receptor isomorph is known to regulate intracellular calcium homeostasis in the brain or other nervous tissues, and the modulation thereof using benzothiazepines has been claimed for treating some neuronal disorders (Marks, A. R. et al. WO2012/037105A1 "Methods and compositions comprising benzazepine derivatives for treating or preventing stress-induced neuronal disorders and diseases"). Furthermore, both RyR1 and RyR2 are expressed in the brain, and there is evidence that calcium regulation and nitro-oxidative stress are involved in various brain disorders and neuronal death (Kakizawa et al., *EMBO J.* 2012, 31, 417-428; Liu X et al., *Cell.* 2012, 150, 1055-1067).

All these prior documents clearly show that the development of compounds which allow regulating or modulating RyR receptors by regulating intracellular calcium levels would offer a useful alternative for the treatment of muscle disorders, as well as heart and neurodegenerative diseases.

BRIEF DESCRIPTION OF THE INVENTION

The authors of the present invention have developed new triazole-derived compounds, particularly, 4-[(phenylthio)alkyl]-1H-1,2,3-triazoles, suitable for modulating RyR receptors regulating calcium function in animal or human cells. Said compounds are referred to as "AHK" in the invention.

As clearly shown in the experimental part, the compounds according to the present invention have the capacity to modulate intracellular calcium homeostasis in dystrophic muscle fibers, reverting the observed intracellular calcium increases. Furthermore, said compounds have a modulating effect on RyR, their capacity for recovering RyR1-calstabin interaction on healthy human myotubes subjected to nitro-oxidative stress having been demonstrated.

In turn, in vivo assays have clearly shown that said compounds furthermore allow improving the grip strength in dystrophic mice, as well as normalizing overexpressed dystrophic genes and reducing dystrophy histopathological markers.

To that end, a first aspect of the invention relates to a 1,4-disubstituted 1,2,3-triazole compound of formula (I):

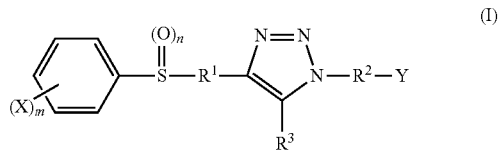

wherein:
$R^1$ is a $C_1$-$C_4$ alkylene biradical optionally substituted with one or more substituents independently selected from the group consisting of $C_{1-4}$ alkyl, $C_{6-10}$ aryl, F, Cl, CN and $NO_2$;
$R^2$ is a $C_1$-$C_6$ alkylene biradical, wherein 1, 2 or 3 —$CH_2$— groups can be optionally replaced with groups selected from —O— and —S—; and wherein the $C_1$-$C_6$ alkylene biradical can be optionally substituted with one or more groups independently selected from $C_{1-4}$ alkyl, allyl, propargyl, hydroxymethyl, 1-hydroxyethyl, 2-hydroxyethyl, 3-aminopropyl, 4-aminobutyl, 3-guanidylpropyl, 3-indolylmethyl, $C_{6-10}$ aryl, benzyl, 4-hydroxybenzyl, $C_{6-10}$ heteroaryl, F, Cl, OH, O($C_{1-4}$ alkyl), CN, $NO_2$, CO($C_{1-4}$ alkyl), $CO_2$($C_{1-4}$ alkyl), —CONH($C_{1-4}$ alkyl), —CON($C_{1-4}$ alkyl)$_2$;
$R^3$ is a group independently selected from H, $C_{1-4}$ alkyl, $C_{6-10}$ aryl, F, Cl, Br, I;
m is selected from 0, 1, 2, 3, 4;
n is selected from 0, 1, 2;
X is independently selected from the group consisting of OH, O($C_{1-4}$ alkyl), O($C_{6-10}$ aryl), $OCF_3$, S($C_{1-4}$ alkyl), S ($C_{6-10}$ aryl), $C_{1-6}$ alkyl, $CF_3$, NHC(O) ($C_{1-4}$ alkyl) and halogen; or two X groups can represent a methylenedioxy, ethylenedioxy or propylenedioxy biradical; and
Y is selected from the group consisting of —OH, —$CO_2H$, —$CO_2$($C_{1-4}$ alkyl), —$CO_2$(allyl), —$CO_2$(benzyl), —$SO_3H$, —$NH_2$, —NH($C_{1-4}$ alkyl), —N($C_{1-4}$ alkyl)$_2$, N($C_{1-4}$ alkyl)$_3$ and —N(heterocyclyl or heteroaryl), where said heterocyclyl or heteroaryl is optionally substituted with a $C_{1-4}$ alkyl group and where the N atom is part of the heterocyclyl or heteroaryl;
or a pharmaceutically acceptable stereoisomer, salt, solvate or complex thereof, or an isotopically labeled derivative or a prodrug thereof.

Another aspect of the invention comprises a method for synthesizing the compounds of formula (I), which comprises:
a) reacting an alkyne of formula (II) with an azide of formula (III),

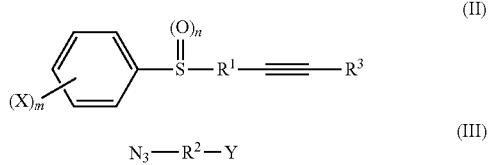

optionally in the presence of a copper catalyst and optionally in the presence of a base, to yield a compound of formula (I) as defined above,
wherein:
groups $R^1$, $R^2$, $R^3$, m, n and X in the compounds of formulae (II)-(III) are as defined above, and
Y is a group as defined above, optionally protected with a carboxyl protecting group, a hydroxyl protecting group or an amino protecting group;
b) when n is 0 in the compound of formula (I) obtained in step a), optionally treating said compound of formula (I) with an oxidizing agent to yield a compound of formula (I) wherein n is 1 or 2, $R^1$, $R^2$, $R^3$, m and X are as defined above, and Y is a group as defined above optionally protected with a carboxyl protecting group, a hydroxyl protecting group or an amino protecting group; and
c) when the compound of formula (I) obtained in step a) or b) has a Y group protected with a protecting group, removing said protecting group to yield a compound of formula (I) wherein $R^1$, $R^2$, $R^3$, m, n, X and Y are as defined above.

Another aspect of the invention relates to pharmaceutical compositions containing a compound of formula (I), defined as indicated above, together with one or more pharmaceutically acceptable excipients or vehicles.

An additional aspect of the present invention relates to the use of a compound of formula (I) as defined above for preparing a medicinal product.

A final aspect of the invention relates to the use of a compound of formula (I) as defined above in the preparation of a medicinal product for the treatment and/or prevention of intracellular calcium concentration dysregulation- or RyR receptor dysfunction-related disorders or diseases, particularly skeletal muscle disorders or diseases, heart disorders or diseases and nervous system disorders or diseases.

Figure 1:
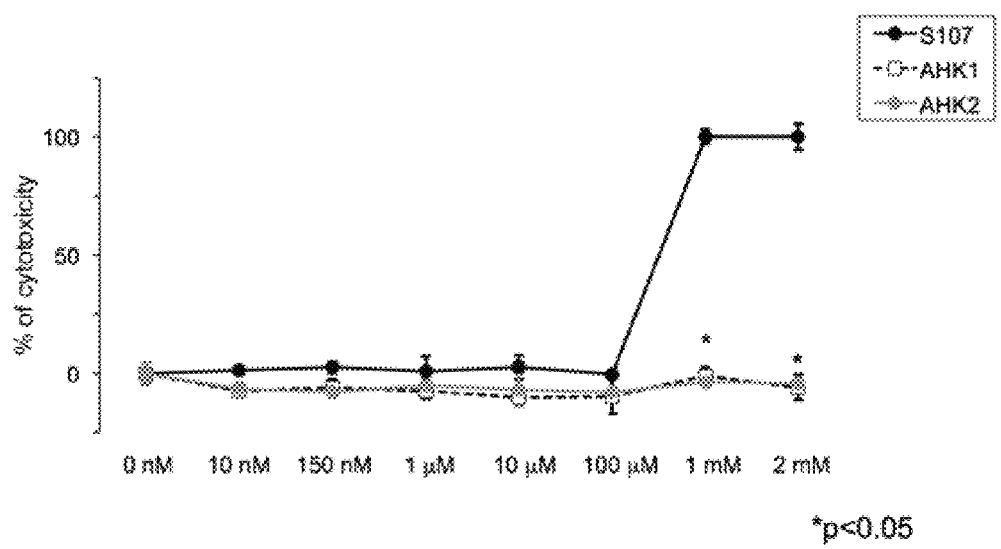
FIG. 1 shows the toxicity curves showing the toxicity of compounds AHK1, AHK2 and S-107 on human myotubes after 24 hours of incubation using the CytoTox 96 colorimetric assay.

Bottom graph: percentage of damaged area in the heart of control mice (Ctl), mdx mice (mdx) and mdx mice treated with AHK2 (mdx AHK2). N=2 mice per group were analyzed; error ±SEM bars.

DETAILED DESCRIPTION OF THE INVENTION

The present invention provides new triazole compounds that are capable of treating or preventing disorders or diseases associated with intracellular calcium dysregulation or RyR receptor dysfunction.

In this sense, as mentioned above the first aspect of the present invention relates to a compound of formula (I):

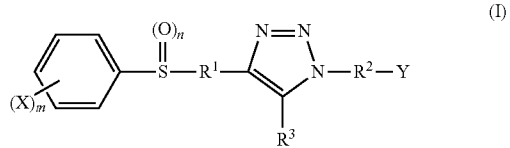

wherein:
$R^1$ is a $C_1$-$C_4$ alkylene biradical optionally substituted with one or more substituents independently selected from the group consisting of $C_{1-4}$ alkyl, $C_{6-10}$ aryl, F, Cl, CN and $NO_2$;
$R^2$ is a $C_1$-$C_6$ alkylene biradical, wherein 1, 2 or 3 —$CH_2$— groups can be optionally replaced with groups selected from —O— and —S—; and wherein the $C_1$-$C_6$ alkylene biradical can be optionally substituted with one or more groups independently selected from $C_{1-4}$ alkyl, allyl, propargyl, hydroxymethyl, 1-hydroxyethyl, 2-hydroxyethyl, 3-aminopropyl, 4-aminobutyl, 3-guanidylpropyl, 3-indolylmethyl, $C_{6-10}$ aryl, benzyl, 4-hydroxybenzyl, $C_{6-10}$ heteroaryl, F, Cl, OH, O($C_{1-4}$ alkyl), CN, $NO_2$, CO($C_{1-4}$ alkyl), $CO_2$ ($C_{1-4}$ alkyl), —CONH($C_{1-4}$ alkyl), —CON($C_{1-4}$ alkyl)$_2$;
$R^3$ is a group independently selected from H, $C_{1-4}$ alkyl, $C_{6-10}$ aryl, F, Cl, Br, I;
m is selected from 0, 1, 2, 3, 4;
n is selected from 0, 1, 2;
X is independently selected from the group consisting of OH, O($C_{1-4}$ alkyl), O($C_{6-10}$ aryl), $OCF_3$, S($C_{1-4}$ alkyl), S ($C_{6-10}$ aryl), $C_{1-6}$ alkyl, $CF_3$, NHC(O) ($C_{1-4}$ alkyl) and halogen; or two X groups can represent a methylenedioxy, ethylenedioxy or propylenedioxy biradical; and
Y is selected from the group consisting of —OH, —$CO_2$H, —$CO_2$($C_{1-4}$ alkyl), —$CO_2$(allyl), —$CO_2$(benzyl), —$SO_3$H, —$NH_2$, —NH($C_{1-4}$ alkyl), —N($C_{1-4}$ alkyl)$_2$ and N($C_{1-4}$ alkyl)$_3$ and —N(heterocyclyl or heteroaryl), where said heterocyclyl or heteroaryl is optionally substituted with a $C_{1-4}$ alkyl group and where the N atom is part of the heterocyclyl or heteroaryl;
or a pharmaceutically acceptable stereoisomer, salt, solvate or complex thereof, or an isotopically labeled derivative thereof, or a prodrug thereof.

In the context of the present invention, the following terms found in the compounds of formula (I) have the meaning indicated below:

The term "alkylene biradical" refers to a biradical formed by a linear or branched hydrocarbon chain consisting of carbon and hydrogen atoms, having no unsaturation and bound at its ends to the rest of the molecule through single bonds, such as, for example, methylene, ethylene, propylene, butylene, etc. Mention of a $C_1$-$C_4$ alkylene biradical refers to said biradical having between 1 and 4 carbon atoms, whereas mention of a $C_1$-$C_6$ alkylene biradical refers to said biradical having between 1 and 6 carbon atoms. The alkylene biradical can be substituted as specified in the definitions of the $R^1$ and $R^2$ substituents in the compound of formula (I).

The term "alkyl" refers to a radical formed by a linear or branched hydrocarbon chain consisting of carbon and hydrogen atoms, which does not contain any saturation and is bound to the rest of the molecule by means of a single bond, for example, methyl, ethyl, n-propyl, i-propyl, n-butyl, t-butyl, n-pentyl, etc. Mention of a $C_1$-$C_4$ alkyl refers to said radical having between 1 and 4 carbon atoms.

The term "$C_6$-$C_{10}$ aryl" refers to a radical formed by a 6 to 10-membered aromatic ring consisting of carbon and hydrogen atoms, preferably a phenyl radical.

The term "$C_6$-$C_{10}$ heteroaryl" refers to a radical formed by a 6 to 10-membered aromatic ring consisting of carbon and hydrogen atoms and one or more heteroatoms selected from O, N and S.

The term "—N(heterocyclyl)" refers to a radical formed by a 5 to 7-membered cycle consisting of carbon and hydrogen atoms and one or more heteroatoms selected from O, N and S, at least one of them being N and the latter being bound directly to the $R^2$ radical.

The term "—N(heteroaryl)" refers to a radical formed by a 6 to 10-membered aromatic ring consisting of carbon and hydrogen atoms and one or more heteroatoms selected from O, N and S, at least one of them being N and the latter being bound directly to the $R^2$ radical.

The term "allyl" refers to a radical of formula —$CH_2$—CH=$CH_2$.

The term "halogen" refers to F, Cl, Br or I.

The expression "isotopically labeled derivative" refers to a compound of formula (I) wherein at least one of its atoms is isotopically enriched. For example, compounds of formula (I) in which a hydrogen is replaced with a deuterium or tritium, a carbon is replaced with a $^{13}C$ or $^{14}C$ enriched atom, or a nitrogen is replaced with a $^{15}N$ enriched atom, are within the scope of this invention.

The term "pharmaceutically acceptable salts or solvates" refers to any pharmaceutically acceptable salt, ester, solvate, or any other compound which, when administered to the recipient, is capable of providing (directly or indirectly) a compound of formula (I) as described in the present document. The salts can be prepared by means of methods known in the state of the art.

For example, pharmaceutically acceptable salts of the compounds provided in the present document are synthesized from the previously described basic or acidic unit-containing compound by means of conventional chemical methods. Such salts are generally prepared, for example, by reacting free acid or base forms of these compounds with a stoichiometric amount of the suitable base or acid in water or in an organic solvent or in a mixture of both. Non-aqueous media such as ether, ethyl acetate, ethanol, isopropanol or acetonitrile are generally preferred. Examples of acid addition salts include mineral acid addition salts such as, for example, hydrochloride, hydrobromide, hydroiodide, sulfate, nitrate, phosphate, and organic acid addition salts such as, for example, acetate, maleate, fumarate, citrate, oxalate, succinate, tartrate, malate, mandelate, methanesulfonate and p-toluenesulfonate. Examples of alkaline addition salts include inorganic salts such as, for example, sodium, potassium, calcium, ammonium, magnesium, aluminum and lithium, and organic alkaline salts such as, for example, ethylenediamine, ethanolamine, N,N-dialkylenethanolamine, glucamine and basic amino acid salts.

Solvates refer to a salt of the compound of formula (I) in which the molecules of a pharmaceutically suitable solvent are incorporated in the crystal lattice. Solvation methods are generally known in the state of the art. Examples of pharmaceutically suitable solvents are ethanol, water and the like. In a particular embodiment, the solvate is a hydrate.

The compounds of formula (I) or the salts or solvates thereof are preferably in a pharmaceutically acceptable form or a substantially pure form. A pharmaceutically acceptable form is understood, inter alia, as having a pharmaceutically acceptable level of purity, excluding normal pharmaceutical additives such as diluents and excipients, and without including any material considered toxic at normal dosage levels. The levels of purity for the drug are preferably above 50%, more preferably above 70%, and even more preferably above 90%. In a preferred embodiment, it is above 95% of the compound of formula (I) or the salts or solvates thereof.

The compounds of the present invention represented by formula (I) described above can include any stereoisomer depending on the presence of chiral centers, including enantiomers and diastereoisomers. The individual isomers, enantiomers or diastereómeros and mixtures thereof are within the scope of the present invention.

The term "prodrug" is used in its broadest sense and comprises those derivatives that are converted in vivo into the compounds of the invention. Such derivatives include, depending on the functional groups present in the molecule, and without limitation, esters, amino acid esters, phosphate esters, metal salt sulfonate esters, carbamates and amides. Examples of methods for producing a prodrug of a given active compound are known by a person skilled in the art and can be found, for example, in Krogsgaard-Larsen et al. "Textbook of Drug Design and Discovery" Taylor & Francis (April 2002).

In one variant (A) of the present invention, the $R^1$ radical is —$CH_2$—.

In a preferred embodiment of said variant (A), $R^2$ is a $C_{1-4}$ alkylene biradical optionally substituted with one or two substituents independently selected from the group consisting of methyl, ethyl, propyl, isopropyl, allyl, propargyl, butyl, isobutyl, sec-butyl, tert-butyl, hydroxymethyl, 1-hydroxyethyl, 2-hydroxyethyl, 3-aminopropyl, 4-aminobutyl, 3-guanidylpropyl, 3-indolylmethyl, phenyl, 1-naphthyl, 2-naphthyl, benzyl, 4-hydroxybenzyl, and $C_{6-10}$ heteroaryl.

More preferably, $R^2$ is a —$CH_2$— or —$CH_2$—$CH_2$— biradical, optionally substituted with one or two substituents independently selected from the group consisting of methyl, isopropyl, isobutyl and benzyl. Even more preferably, $R^2$ is a —$CH_2$— biradical optionally substituted with two methyl substituents or with one substituent selected from the group consisting of isopropyl, isobutyl and benzyl, or $R^2$ is a —$CH_2$—$CH_2$— biradical. Also preferably, $R^2$ is a —$CH_2$— or —$CH_2$—$CH_2$-biradical.

In another preferred embodiment of said variant (A), $R^3$ is H.

In another preferred embodiment of said variant (A), m is 1.

In another preferred embodiment of said variant (A), n is 0.

In another preferred embodiment of said variant (A), X is —$O(C_{1-4}$ alkyl) or halogen, more preferably a methoxy group in meta or para position or chlorine.

In another preferred embodiment of said variant (A), Y is selected from the group consisting of $CO_2H$, $CO_2Me$, $NH_2$, —NHMe, —$NMe_2$, —$NMe_3$, —NHEt, —$NEt_2$, —$NEt_3$,

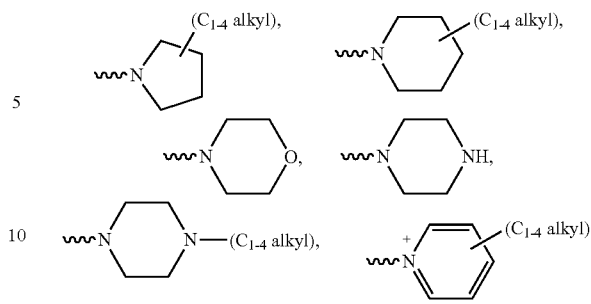

or a pharmaceutically acceptable salt of said groups.

More preferably, Y is selected from the group consisting of $CO_2H$, $CO_2Me$, $NH_2$, —NHMe, —$NMe_2$, —$NMe_3$, —NHEt, —$NEt_2$, —$NEt_3$, pyrrolidin-1-yl, piperidin-1-yl, morpholin-4-yl, 4-piperazin-1-yl, 4-methyl-piperazin-1-yl, pyridin-1-yl, more preferably $CO_2H$ and —$NMe_2$, even more preferably Y is —$CO_2H$ or a pharmaceutically acceptable salt thereof.

Within variant (A), the compounds of formula (I) are selected from the group consisting of:
1-carboxymethyl-4-[3-(methoxy)phenylthiomethyl]-1H-1,2,3-triazole,
1-[2-(N,N-dimethylamino)ethyl]-4-[4-(methoxy)phenylthiomethyl]-1H-1,2,3-triazole,
1-carboxymethyl-4-[4-(methoxy)phenylthiomethyl]-1H-1,2,3-triazole,
(S)-1-(1-carboxy-2-phenylethyl)-4-[3-(methoxy)phenylthiomethyl]-1H-1,2,3-triazole,
(R)-1-(1-carboxy-2-phenylethyl)-4-[3-(methoxy)phenylthiomethyl]-1H-1,2,3-triazole,
(S)-1-(1-carboxy-3-methylbutyl)-4-[3-(methoxy)phenylthiomethyl]-1H-1,2,3-triazole,
(R)-1-(1-carboxy-3-methylbutyl)-4-[3-(methoxy)phenylthiomethyl]-1H-1,2,3-triazole,
(S)-1-(1-carboxy-2-methylpropyl)-4-[3-(methoxy)phenylthiomethyl]-1H-1,2,3-triazole,
(R)-1-(1-carboxy-2-methylpropyl)-4-[3-(methoxy)phenylthiomethyl]-1H-1,2,3-triazole,
1-(1-carboxy-1-methylethyl)-4-[3-(methoxy)phenylthiomethyl]-1H-1,2,3-triazole,
1-(2-hydroxyethyl)-4-[4-(methoxy)phenylthiomethyl]-1H-1,2,3-triazole,
1-methoxycarbonylmethyl-4-(phenylsulfinylmethyl)-1H-1,2,3-triazole, and
1-carboxymethyl-4-[3-(methoxy)phenylsulfonylmethyl]-1H-1,2,3-triazole,
1-carboxymethyl-4-[3-(chloro)phenylthiomethyl]-1H-1,2,3-triazole,
or a salt thereof.

In a variant (B) of the present invention, the $R^1$ radical is —$CH_2$—.

In a preferred embodiment of said variant (B), $R^2$ is a $C_{1-4}$ alkylene biradical wherein one or two —$CH_2$— groups are replaced with —O—, and where said $C_1$-$C_4$ alkylene biradical is optionally substituted with one or two $C_1$-$C_4$ alkyl groups, preferably selected from methyl, ethyl, n-propyl, isopropyl, n-butyl and tert-butyl.

More preferably, $R^2$ is a —$CH_2$— or —$CH_2$—$CH_2$— biradical, optionally substituted with one or two substituents independently selected from the group consisting of methyl, isopropyl and isobutyl. Even more preferably, $R^2$ is a —$CH_2$-biradical optionally substituted with two methyl substituents or with one substituent selected from the group consisting of isopropyl and isobutyl, or $R^2$ is a —$CH_2$—$CH_2$— biradical.

In another preferred embodiment of said variant (B), $R^3$ is H.

In another preferred embodiment of said variant (B), m is 1.

In another preferred embodiment of said variant (B), n is 0.

In another preferred embodiment of said variant (B), X is —O($C_{1-4}$ alkyl) or halogen, more preferably a methoxy group in meta or para position or chlorine.

In another preferred embodiment of said variant (B), Y is selected from the group consisting of $NH_2$, —NH($C_2$-$C_4$ alkyl), —N($C_1$-$C_4$ alkyl)$_2$, —N($C_1$-$C_4$ alkyl)$_3$,

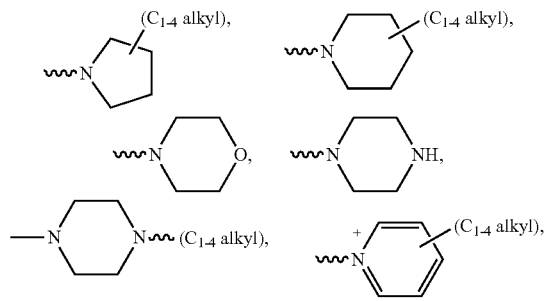

More preferably Y is selected from —$NH_2$, —NHMe, —$NMe_2$, —$NMe_3$, —NHEt, —$NEt_2$, —$NEt_3$, pyrrolidin-1-yl, piperidin-1-yl, morpholin-4-yl, 4-piperazin-1-yl, 4-methyl-piperazin-1-yl, pyridin-1-yl or a pharmaceutically acceptable salt of said groups. More preferably, Y is —$NMe_2$, or a pharmaceutically acceptable salt thereof.

In a variant (C) of the present invention, the $R^1$ radical is —$CH_2$—.

In a preferred embodiment of said variant (C), $R^2$ is a $C_{1-4}$ alkylene biradical optionally substituted with one or two substituents independently selected from the group consisting of methyl, ethyl, propyl, isopropyl, allyl, propargyl, butyl, isobutyl, sec-butyl, tert-butyl, hydroxymethyl, 1-hydroxyethyl, 2-hydroxyethyl, 3-aminopropyl, 4-aminobutyl, 3-guanidylpropyl, 3-indolylmethyl, phenyl, 1-naphthyl, 2-naphthyl, benzyl, 4-hydroxybenzyl, and $C_{6-10}$ heteroaryl.

More preferably, $R^2$ is a —$CH_2$— or —$CH_2$—$CH_2$— biradical, optionally substituted with one or two substituents independently selected from the group consisting of methyl, isopropyl, isobutyl and benzyl. Even more preferably, $R^2$ is a —$CH_2$— biradical optionally substituted with two methyl substituents or with one substituent selected from the group consisting of isopropyl, isobutyl and benzyl, or $R^2$ is a —$CH_2$—$CH_2$— biradical. Also preferably, $R^2$ is a —$CH_2$— or —$CH_2$—$CH_2$-biradical.

In another preferred embodiment of said variant (C), $R^3$ is H.

In another preferred embodiment of said variant (C), m is 1.

In another preferred embodiment of said variant (C), n is 0.

In another preferred embodiment of said variant (C), X is —O($C_{1-4}$ alkyl) or halogen, more preferably a methoxy group in meta or para position or chlorine.

In another preferred embodiment of said variant (C), Y is selected from the group consisting of $CO_2H$, $CO_2(C_1$-$C_4$ alkyl), $NH_2$, —NH($C_1$-$C_4$ alkyl), —N($C_1$-$C_4$ alkyl)$_2$, —N($C_1$-$C_4$ alkyl)$_3$,

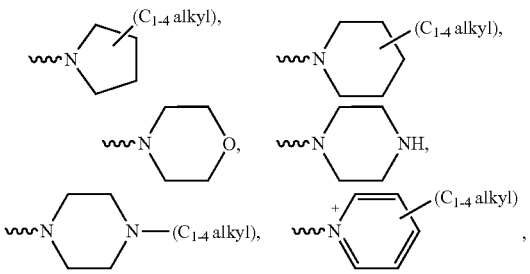

or a pharmaceutically acceptable salt of said groups.

More preferably Y is selected from —$NH_2$, —NHMe, —$NMe_2$, —$NMe_3$, —NHEt, —$NEt_2$, pyrrolidin-1-yl, piperidin-1-yl, morpholin-4-yl, 4-piperazin-1-yl, 4-methyl-piperazin-1-yl, pyridin-1-yl or a pharmaceutically acceptable salt of said groups.

More preferably, Y is selected from the group consisting of $CO_2H$ and —$NMe_2$ or a pharmaceutically acceptable salt thereof.

Method for Obtaining the Compounds of the Invention

The compounds of formula (I) of the present invention can be prepared by means of a method which comprises reacting an alkyne of formula (II) with an azide of formula (III):

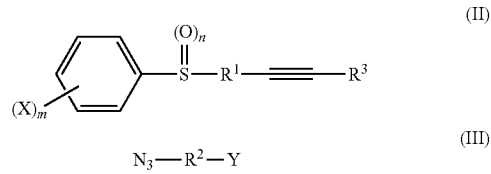

wherein $R^1$, $R^2$, $R^3$, m, n and X in the compounds of formulae (II)-(III) are as defined for the compounds of formula (I), and wherein Y is a group as defined for the compounds of formula (I), optionally protected with a carboxyl protecting group, a hydroxyl protecting group or an amino protecting group, depending on the nature of said Y group.

This reaction can be carried out in the presence of a copper catalyst, such as copper(II) sulfate/sodium ascorbate, copper(I) iodide or copper(I) acetate, for example.

Furthermore, in a preferred embodiment, the reaction between the compound of formula (II) and the compound of formula (III) is performed in the presence of a base, such as sodium acetate, diisopropylamine or triethylamine, for example.

In a particular embodiment, when n is 0, the compound of formula (I) obtained according to the preceding method can be treated with an oxidizing agent to yield a compound of formula (I) wherein n is 1 or 2.

Examples of oxidizing agents include, for example, 3-chloroperbenzoic acid or tert-butyl hydroperoxide.

In another particular embodiment, when the compound of formula (I) obtained according to the preceding method has a Y group protected with a protecting group, said protecting group is removed to yield a compound of formula (I) wherein $R^1$, $R^2$, $R^3$, m, n, X and Y are as defined for the compound of formula (I). The protecting group can be removed following methods commonly known for a person skilled in organic synthesis.

Pharmaceutical Compositions

The present invention further provides pharmaceutical compositions comprising a compound of formula (I), or a pharmaceutically acceptable stereoisomer, salt, solvate or complex thereof, or an isotopically labeled derivative thereof, or a prodrug thereof; and one or more pharmaceutically acceptable excipients or vehicles.

The pharmaceutically acceptable vehicle must be acceptable in the sense of being compatible with other ingredients of the composition and not being harmful to the receiver thereof. Said pharmaceutically acceptable vehicle can be selected from organic and inorganic materials that are used in pharmaceutical formulations and incorporated as analgesic agents, pH regulators, linkers, disintegrants, diluents, emulsifiers, fillers, glidants, solubilizers, stabilizers, suspension agents, tonicity agents and thickeners. Pharmaceutical additives such as antioxidants, aromatic agents, dyes, aroma enhancing agents, preservatives and sweeteners can furthermore be added.

Examples of pharmaceutically acceptable vehicles include, among others, carboxymethyl cellulose, crystalline cellulose, glycerin, acacia gum, lactose, magnesium stearate, methylcellulose, saline solution, sodium alginate, sucrose, starch, talc and water.

The pharmaceutical formulations of the present invention are prepared by methods well known in the pharmaceutical art. For example, the compounds of formula (I) are mixed with a pharmaceutically acceptable excipient or vehicle, as a suspension or solution. The choice of the vehicle is determined by the solubility and the chemical nature of the compounds, the chosen route of administration and standard pharmaceutical practice.

The compounds or compositions of the present invention can be administered to a human or animal subject by means of any known method including, without limitation, oral administration, sublingual or buccal administration, parenteral administration, transdermal absorption, by nasal instillation or inhalation, vaginal, rectal and intramuscular administration.

In a particular embodiment, the administration is performed parenterally, such as by means of subcutaneous injection, intramuscular injection, intraperitoneal injection, intravenous injection, for example. For parenteral administration, the compounds of the invention are combined with a sterile aqueous solution which is isotonic with the subject's blood. A formulation of this type is prepared by dissolving the solid active ingredient in water containing physiologically compatible substances, such as sodium chloride, glycine and the like, and having a buffered pH compatible with physiological conditions. Said formulation is presented in single- or multidose containers, such as closed vials or ampoules.

In another particular embodiment, the administration is performed orally. In that case, the formulation of the compounds of the invention can be presented in the form of capsules, tablets, powders, granules, or as a suspension or solution. Said formulation can include conventional additives, such as lactose, mannitol, starch, etc.; binders, such as crystalline cellulose, cellulose derivatives, acacia gum, cornstarch or gelatins; disintegrants, such as cornstarch and potato starch or sodium carboxymethyl cellulose; lubricants, such as talc or magnesium stearate.

Applications

The compounds of the present invention are suitable for modulating RyR receptors which regulate calcium function in animal or human cells, so they are capable of treating or preventing disorders or diseases associated with intracellular calcium dysregulation fundamentally caused by RyR receptor dysfunction.

"Intracellular calcium dysregulation" must be understood as an abnormal regulation of calcium levels and calcium fluxes in cells.

Therefore, an increase in the intracellular calcium ($Ca^{2+}$) concentration under resting conditions leads to damage to toxic muscle cells (myofibers) and the simultaneous activation of $Ca^{2+}$-dependent proteases, such as calpain. Given that calpain activity increases in necrotic muscle fibers of mdx mice and that calpain dysfunction leads to limb-girdle muscular dystrophy, preventing the activity of calcium-dependent proteases by inhibiting intracellular $Ca^{2+}$ increments, allows preventing muscle atrophy and therefore treating diseases such as Duchenne muscular dystrophy or Becker muscular dystrophy.

The in vitro assays performed with the compounds of the invention have shown the capacity of these compounds to revert intracellular calcium increases back in muscle fibers, suggesting that these compounds carry out this reversion through a mechanism involving RyR channel modulation. Furthermore, said compounds have also shown capacity to reduce the number of genes overexpressed in dystrophic mdx muscle by half, one of said genes being linked to skeletal muscle loss or atrophy.

RyR receptors regulating intracellular calcium function include RyR1, RyR2 and RyR3, as well as an RyR protein or an RyR analogue. An RyR analogue refers to a functional variant of an RyR protein with biological activity having a homology of 60% or greater in the amino acid sequence with the RyR protein.

In the context of the present invention, "RyR biological activity" must be understood as the activity of the protein or peptide showing the capacity to physically associate itself with or bind to FKBP 12 (calstabin-1) in the case of RyR1 and RyR3, and to FKBP12.6 (calstabin-2) in the case of RyR2, under the assay conditions described herein.

The compounds of the present invention can be used for limiting or preventing a drop in the RyR-bound FKBP (calstabin) level in the cells of a subject. Based on what is described in the preceding paragraph, RyR-bound FKBP refers to RyR1-bound FKBP12 (calstabin-1), RyR2-bound FKBP 12.6 (calstabin-2) and RyR3-bound FKBP12 (calstabin-1).

A drop in the RyR-bound FKBP level in the cells of a subject is limited or prevented when said drop is, in any way, stopped, blocked, hindered, obstructed or reduced by means of administering the compounds of the invention, such that the RyR-bound FKBP level in the cells of a subject is greater than what it would be otherwise in the absence of the administered compound.

The RyR-bound FKBP level in a subject is detected using standard assays or techniques known by a person skilled in the art, such as immunological techniques, hybridization analysis, immunoprecipitation, Western blot analysis, fluorescence imaging and/or radiation detection techniques, as well as any other assays or techniques, like the ones disclosed in the experimental part of the present document.

In a particular embodiment, the drop in the RyR-bound FKBP (calstabin) level occurs as a result of subjecting the cells from a subject to nitro-oxidative stress. In fact, the experimental assays performed with the compounds of the invention have clearly shown that said compounds allow minimizing the degenerative effects of nitro-oxidative stress on healthy human myotubes through an increase in RyR1-calstabin1 interaction affinity.

Accordingly, it has been demonstrated that the compounds of the invention prevent disorders or conditions involving RyR receptor modulation or intracellular calcium increase, which thereby allows regulating the levels thereof. Examples of said disorders or conditions include skeletal muscle disorders and diseases (related to RyR1 modulation), heart disorders and diseases (related to RyR2 modulation) and nervous system disorders and diseases (related to RyR1, RyR2 or RyR3 modulation).

Therefore, an additional aspect of the present invention relates to the use of the compounds of formula (I), or a pharmaceutically acceptable stereoisomer, salt, solvate or complex thereof, or an isotopically labeled derivative thereof, or a prodrug thereof, in the preparation of a medicinal product intended for the treatment and/or prevention of skeletal muscle disorders and diseases, heart disorders and diseases and nervous system disorders and diseases.

In a particular embodiment, the skeletal muscle disorders and diseases are selected from muscular dystrophies, congenital myopathies, metabolic myopathies and muscle atrophy. Preferably, said skeletal muscle disorder or disease is Duchenne muscular dystrophy or Becker muscular dystrophy.

In another particular embodiment, the heart disorders and diseases are selected from heart failure, cardiac ischemia, cardiac arrhythmias and cardiomyopathies.

In another particular embodiment, the nervous system disorders and diseases are selected from stroke, Alzheimer's disease, frontotemporal dementia and cognitive impairment.

In a preferred embodiment, the compounds according to variant (A) of the present invention are those used in the preparation of a medicinal product intended for the treatment of skeletal muscle disorders and diseases, as well as for the treatment of heart disorders and diseases, such as those described above.

In another preferred embodiment, the compounds according to variant (B) of the present invention are those used in the preparation of a medicinal product intended for the treatment of nervous system disorders and diseases such as those described above.

An additional aspect of the present invention relates to a compound of formula (I), or a pharmaceutically acceptable stereoisomer, salt, solvate or complex thereof, or an isotopically labeled derivative thereof, or a prodrug thereof, for the use thereof in the treatment and/or prevention of skeletal muscle disorders and diseases, heart disorders and diseases and nervous system disorders and diseases.

Another aspect of the invention relates to a method for the treatment and/or prevention of skeletal muscle disorders and diseases, heart disorders and diseases and nervous system disorders and diseases, which method comprises administering to a patient in need thereof a therapeutically effective amount of a compound of formula (I), or a pharmaceutically acceptable stereoisomer, salt, solvate or complex thereof, or an isotopically labeled derivative thereof, or a prodrug thereof.

"Therapeutically effective" amount must be understood as the amount sufficient to achieve beneficial or desired results, the response being preventive and/or therapeutic, preventing or substantially mitigating unwanted side effects.

In a particular embodiment, the compounds of the present invention are administered to a subject in an amount effective for modulating abnormal intracellular calcium concentrations. This amount can be readily determined by a person skilled in the area using known methods. For example, the release of intracellular calcium through RyR channels can be quantified using calcium-sensitive fluorescent dyes, such as Fluo-3 or Fura-2 and monitoring calcium-dependent fluorescence signals with a photomultiplier tube and suitable software (Brillantes, et al. *Cell*, 1994, 77, 513-523, "Stabilization of calcium release channel (ryanodine receptor) function by FK506-binding protein"; Gillo, et al. *Blood*, 1993, 81, 783-792).

The concentration of the compounds of the invention in the serum of a human or animal subject can be determined following methods known in the art (Thebis, M. et al. *Drug Test. Analysis* 2009, 1, 32-42 "Screening for the calstabin-ryanodine receptor complex stabilizers JTV-519 and S-107 in doping control analysis"). The administered amount of compounds of formula (I) which is effective for limiting or preventing abnormal intracellular calcium levels will depend on the relative efficacy of the chosen compound, the seriousness of the treated disorder and the weight of the affected subject. Nevertheless, the compounds will typically be administered once a day or more, for example 1, 2, 3 or 4 times daily, with total typical daily doses in the range of between about 1 mg/kg/day and 100 mg/kg/day, and more preferably between 10 mg/kg/day and 40 mg/kg/day, or an amount sufficient for achieving serum levels between about 1 ng/ml and 500 ng/ml.

The compounds of formula (I) can be used alone, combined with one another, or combined with other drugs having therapeutic activity including, but are not limited to, mRNA exonic splicing enhancer, gene transcription modulators, diuretics, anticoagulants, platelet agents, antiarrhythmics, inotropic agents, chronotropic agents, α- and β-blockers, angiotensin inhibitors and vasodilators.

Said drugs can be part of the same composition, or be provided as a separate composition, for administration at the same time or at a different time.

The present invention also includes an in vitro method for determining the capacity of a compound to modulate intracellular calcium levels and prevent calstabin dissociation from the RyR protein complex, where said method comprises: (a) obtaining or generating a cell culture containing RyR receptors; (b) contacting the cells with the compound to be assayed; (c) exposing the cells to one or more known conditions which alter intracellular calcium regulation or generate post-translational modifications in the RyR receptor; (d) determining if said compound modulates intracellular calcium levels; and (e) determining if said compound limits or prevents calstabin dissociation from the RyR protein complex.

In a particular embodiment, the conditions which alter intracellular calcium regulation or generate post-translational modifications in the RyR receptor are oxidative stress or nitrosative stress.

The present invention also contemplates a method for the diagnosis of a disorder or disease, where said method comprises:
  obtaining a tissue or cell sample containing RyR receptors from a subject;
  incubating the tissue or cell sample obtained in step a) with a compound of formula (I), and
  determining if:
    (a) there is an increase in RyR-calstabin interaction with respect to RyR-calstabin interaction in control cells or tissue;
    or
    (b) there is a drop in intracellular calcium levels compared with the absence of such drop in control cells or tissue;

where an increase in RyR-calstabin interaction in (a) or a drop in intracellular calcium levels in (b), indicates the presence of a disorder or disease in the subject.

In a particular embodiment, the compound of formula (I) used in the diagnostic method is a compound according to variant (C) of the present invention.

In another particular embodiment, the tissue sample is a muscle tissue sample.

In a particular embodiment, when RyR is RyR1, the disorder or disease to be diagnosed is a skeletal muscle disorder or disease.

In a particular embodiment, when RyR is RyR2, the disorder or disease to be diagnosed is a heart disorder or disease.

In a particular embodiment, when RyR is RyR1, RyR2 or RyR3, the disorder or disease to be diagnosed is a nervous system disorder or disease.

The increase in RyR-calstabin interaction and the drop in intracellular calcium levels can be measured by means of techniques known by a skilled person, such as immunoprecipitation, in situ proximity ligation assays (PLAs) and real time calcium imaging using fluorescent probes.

EXAMPLES

The acronyms of the compounds, reagents, solvents or techniques used are defined as follows:

AHK1: compound according to formula (I) containing groups: $R^1=R^2=-CH_2-$; $R^3=H$; m=1; n=0; X=3-MeO; $Y=CO_2H$, AHK2: compound according to formula (I) containing groups: $R^1=-CH_2-$; $R^2=-CH_2CH_2-$; $R^3=H$; m=1; n=0; X=4-MeO; $Y=NMe_2$, S-107: compound used for comparison purposes in the biological assays that have been performed, the structure of which is found in the background section of this document.

$^tBuOH$: tert-butanol,

DAPI: 4',6-diamino-2-phenylindol,

ESI: electrospray ionization,

EtOAc: ethyl acetate,

HRMS: high-resolution mass spectrometry,

IR: infrared spectroscopy, mdx: animal model of X-linked Duchenne muscular dystrophy, MP: melting point, NMR: nuclear magnetic resonance, SIN1: 3-morpholino-sydnonimine, peroxynitrite- and nitric oxide-generating agent.

THF: tetrahydrofuran,

TBTA: tris[(1-benzyl-1H-1,2,3-triazol-4-yl)methyl]amine.

The following examples are provided for illustrative purposes and do not seek to limit the present invention.

Example 1: 1-methoxycarbonylmethyl-4-[4-(methoxy)phenylthiomethyl]-1H-1,2,3-triazole

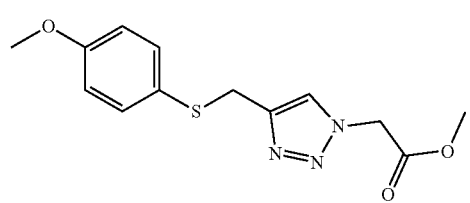

A solution of 1-(4-methoxyphenylthio)-2-propyne (2 mmol, 356 mg), methyl azidoacetate (2.00 mmol, 230 mg) and TBTA (catalyst) in THF/tBuOH (1:1, 4 mL) was prepared under a nitrogen atmosphere. Two degassed aqueous solutions of $CuSO_4$ (0.4 mmol, 63 mg) in $H_2O$ (1 mL) and sodium ascorbate (0.8 mmol, 158 mg) in $H_2O$ (1 mL) were then added and the mixture was stirred at room temperature overnight. Upon completion of the reaction, the solvent was evaporated, a 28% aqueous ammonium solution (10 mL) was added and the product was extracted with $CH_2Cl_2$ (3×20 mL). The pooled organic extracts were dried ($MgSO_4$) and the solvent was evaporated at reduced pressure. The product was purified by column chromatography (silica gel; 1:3 EtOAc/hexane). Yield: 477 mg (78%). Yellowish oil. IR (cm$^{-1}$): 2953, 2837 (C—H), 1750 (C=O), 1219, 1174 (triazole). $^1H$ NMR (500 MHz, $CDCl_3$): δ 7.38 (s, 1H), 7.30 (d, J=8.7 Hz, 2H), 6.81 (d, J=8.7 Hz, 2H), 5.09 (s, 3H), 4.12 (s, 2H), 3.78 (s, 3H), 3.77 (s, 3H). $^{13}C$ NMR (125 MHz, $CDCl_3$): δ 166.7, 159.4, 145.8, 134.0, 125.4, 123.5, 114.7, 55.4, 53.1, 50.8, 30.9. HRMS (ESI+, m/z) for $C_{13}H_{16}N_3O_3S$, calculated: 294.0912; detected: 294.0916.

Example 2: 1-methoxycarbonylmethyl-4-[3-(methoxy)phenylthiomethyl]-1H-1,2,3-triazole

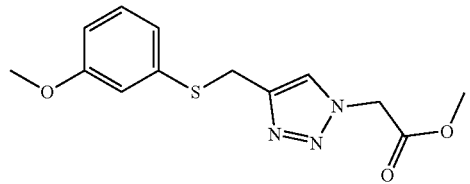

The method of Example 1 was followed starting from 1-(3-methoxyphenylthio)-2-propyne (2.00 mmol, 356 mg) and methyl azidoacetate (2.00 mmol, 230 mg). Yield: 537 mg (88%). Yellowish oil. IR (cm$^{-1}$): 2953, 2837 (C—H), 1749 (C=O), 1220, 1180 (triazole). $^1H$ NMR (500 MHz, $CDCl_3$): δ 7.51 (s, 1H), 7.18 (t, J=8.0 Hz, 1H), 6.92 (d, J=7.7 Hz, 1H), 6.90-6.87 (m, 1H), 6.73 (dd, J=8.2, 1.8 Hz, 1H) 5.11 (s, 2H), 4.26 (s, 2H), 3.78 (s, 3H), 3.77 (s, 3H). $^{13}C$ NMR (125 MHz, $CDCl_3$): δ 166.7, 159.9, 145.7, 136.8, 129.9, 123.6, 121.5, 114.6, 112.5, 55.4, 53.1, 50.8, 28.7. HRMS (ESI+, m/z) for $C_{13}H_{16}N_3O_3S$, calculated: 294.0912; detected: 294.0917.

Example 3: (S)-1-(1-methoxycarbonyl-2-phenyl-ethyl)-4-[3-(methoxy)phenylthiomethyl]-1H-1,2,3-triazole

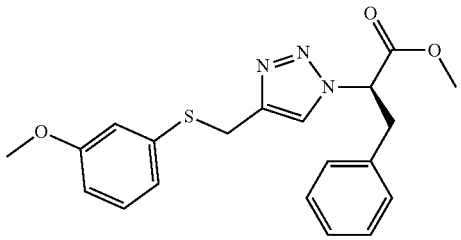

The method of Example 1 was followed starting from 1-(3-methoxyphenylthio)-2-propyne (2.00 mmol, 384 mg)

and (S)-2-azido-3-phenylpropanoic acid methyl ester (2.00 mmol, 358 mg). Yield: 668 mg (87%). Yellowish oil. $[\alpha]_D^{25}=-56.1°$ (c. 1.01 g/100 mL, CH$_2$Cl$_2$). IR (cm$^{-1}$): 2952, 2836 (C—H), 1744 (C=O), 1228, 1172 (triazole). $^1$H NMR (400 MHz, CDCl$_3$): δ 7.47 (s, 1H), 7.27-6.62 (m, 9H), 5.50 (dd, J=8.5, 6.2 Hz, 1H), 4.12 (q, J=14.9 Hz, 2H), 3.75 (s, 3H), 3.73 (s, 3H), 3.46 (dd, J=14.0, 5.8 Hz, 1H), 3.36 (dd, J=13.9, 9.2 Hz, 1H). $^{13}$C NMR (101 MHz, CDCl$_3$): δ 168.6, 159.9, 145.1, 136.8, 134.7, 129.9, 128.9, 127.6, 122.4, 121.5, 114.5, 112.5, 64.3, 55.4, 53.2, 38.9, 28.7. HRMS (ESI+, m/z) for C$_{20}$H$_{22}$N$_3$O$_3$S, calculated: 384.1382; detected: 384.1392.

Example 4: (R)-1-(1-methoxycarbonyl-2-phenyl-ethyl)-4-[3-(methoxy)phenylthiomethyl]-1H-1,2,3-triazole

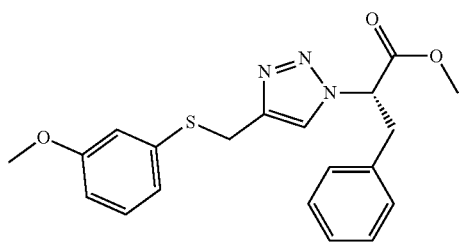

The method of Example 1 was followed starting from 1-(3-methoxyphenylthio)-2-propyne (2.00 mmol, 384 mg) and (R)-2-azido-3-phenylpropanoic acid methyl ester (2.00 mmol, 358 mg). Yield: 653 mg (85%). Yellowish oil. $[\alpha]_D^{25}=+39.4°$ (c. 2.71 g/100 mL, CH$_2$Cl$_2$). HRMS (ESI+, m/z) for C$_{20}$H$_{22}$N$_3$O$_3$S, calculated: 384.1382; detected: 384.1382. The NMR data was identical to that of Example 3.

Example 5: (S)-1-(1-methoxycarbonyl-3-methyl-butyl)-4-[3-(methoxy)phenylthiomethyl]-1H-1,2,3-triazole

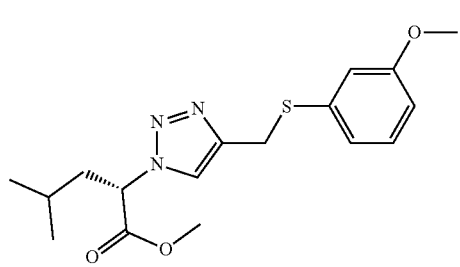 [SMILES: COC(=O)[C@H](CC(C)C)n1cc(CSc2cccc(OC)c2)nn1]

The method of Example 1 was followed starting from 1-(3-methoxyphenylthio)-2-propyne (2.00 mmol, 384 mg) and (S)-2-azido-4-methylpentanoic acid methyl ester (2.00 mmol, 342 mg). Yield: 677.9 mg (97%). Yellowish oil. $[\alpha]_D^{25}=+10.7°$ (c. 1.00 g/100 mL, CH$_2$Cl$_2$). $^1$H NMR (500 MHz, CDCl$_3$): δ 7.51 (s, 1H), 7.16 (t, J=8.0 Hz, 1H), 6.90 (d, J=7.7 Hz, 1H), 6.87 (s, 1H), 6.72 (dd, J=8.2, 1.8 Hz, 1H), 5.38 (t, J=8.0 Hz, 1H), 4.24 (q, J=14.8 Hz, 2H), 3.76 (s, 3H), 3.73 (s, 3H), 1.94 (t, J=7.5 Hz, 2H), 1.19 (dt, J=13.4, 6.7 Hz, 1H), 0.90 (d, J=6.5 Hz, 3H), 0.84 (d, J=6.6 Hz, 3H). $^{13}$C NMR (125 MHz, CDCl$_3$): δ 169.8, 159.9, 145.3, 136.6, 129.8, 122.1, 115.1, 112.7, 61.1, 55.3, 53.1, 41.4, 29.1, 24.7, 22.7, 21.3.

Example 6: (R)-1-(1-methoxycarbonyl-3-methyl-butyl)-4-[3-(methoxy)phenylthiomethyl]-1H-1,2,3-triazole

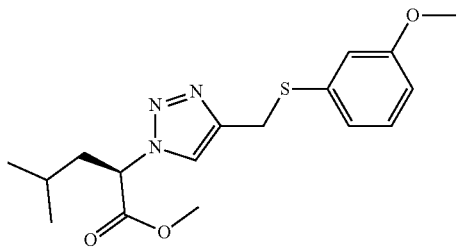 [SMILES: COC(=O)[C@@H](CC(C)C)n1cc(CSc2cccc(OC)c2)nn1]

The method of Example 1 was followed starting from 1-(3-methoxyphenylthio)-2-propyne (2.00 mmol, 384 mg) and (R)-2-azido-4-methylpentanoic acid methyl ester (2.00 mmol, 342 mg). Yield: 653 mg (93%). Yellowish oil. $[\alpha]_D^{25}=-12.1°$ (c. 1.03 g/100 mL, CH$_2$Cl$_2$). The NMR data was identical to that of Example 5.

Example 7: (S)-1-(1-methoxycarbonyl-2-methyl-propyl)-4-[3-(methoxy)phenylthiomethyl]-1H-1,2,3-triazole

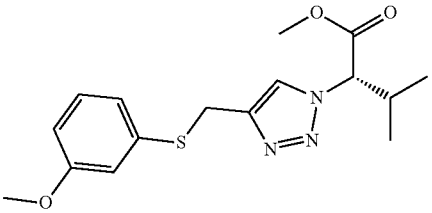 [SMILES: COC(=O)[C@H](C(C)C)n1cc(CSc2cccc(OC)c2)nn1]

The method of Example 1 was followed starting from 1-(3-methoxyphenylthio)-2-propyne (2.00 mmol, 384 mg) and (S)-2-azido-3-methylbutanoic acid methyl ester (2.00 mmol, 314 mg). Yield: 616 mg (92%). Yellowish oil. $[\alpha]_D^{25}=+21.5°$ (c. 1.03 g/100 mL, CH$_2$Cl$_2$). $^1$H NMR (500 MHz, CDCl$_3$): δ 7.63 (s, 1H), 7.16 (t, J=7.9 Hz, 1H), 6.92 (d, J=7.5 Hz, 1H), 6.88 (s, 1H), 6.72 (d, J=6.8 Hz, 1H), 5.06 (d, J=8.7 Hz, 1H), 4.24 (q, J=14.7 Hz, 2H), 3.76 (s, 6H), 2.44-2.30 (m, 1H), 0.96 (d, J=6.6 Hz, 3H), 0.73 (d, J=6.6 Hz, 3H). $^{13}$C NMR (125 MHz, CDCl$_3$): δ 168.8, 159.6, 144.7, 136.3, 129.5, 121.9, 115.0, 112.3, 68.5, 55.0, 52.5, 32.0, 28.8, 18.8, 18.1.

Example 8: (R)-1-(1-methoxycarbonyl-2-methyl-propyl)-4-[3-(methoxy)phenylthiomethyl]-1H-1,2,3-triazole

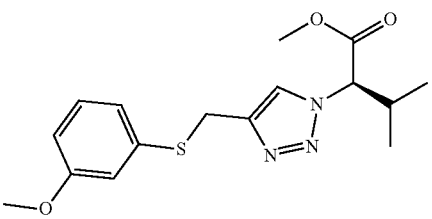 [SMILES: COC(=O)[C@@H](C(C)C)n1cc(CSc2cccc(OC)c2)nn1]

The method of Example 1 was followed starting from 1-(3-methoxyphenylthio)-2-propyne (2.00 mmol, 384 mg) and (R)-2-azido-3-methylbutanoic acid methyl ester (2.00 mmol, 314 mg). Yield: 626 mg (93%). Yellowish oil. $[\alpha]_D^{25}=-19.5°$ (c. 1.06 g/100 mL, $CH_2Cl_2$). The NMR data was identical to that of Example 7.

Example 9: 4-[3-(methoxy)phenylthiomethyl]-1-(1-methyl-1-methoxycarbonylethyl)-1H-1,2,3-triazole

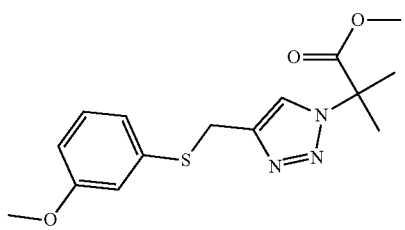

The method of Example 1 was followed starting from 1-(3-methoxyphenylthio)-2-propyne (2.00 mmol, 384 mg) and methyl 2-azidoisobutyrate (2.00 mmol, 386 mg). Yield: 258 mg (40%). Yellowish oil. $^1$H NMR (400 MHz, $CDCl_3$): δ 7.44 (s, 1H), 7.11 (t, J=7.7 Hz, 1H), 6.85 (d, J=7.6 Hz, 1H), 6.82 (s, 1H), 6.67 (d, J=7.6 Hz, 1H), 4.17 (s, 2H), 3.69 (s, 3H), 3.62 (s, 3H), 1.82 (s, 6H). $^{13}$C NMR (101 MHz, $CDCl_3$) δ 171.6, 159.7, 144.3, 136.7, 129.6, 121.6, 121.0, 114.8, 112.3, 64.3, 55.1, 53.1, 28.8, 25.5.

Example 10: 1-(2-hydroxyethyl)-4-[4-(methoxy)phenylthiomethyl]-1H-1,2,3-triazole

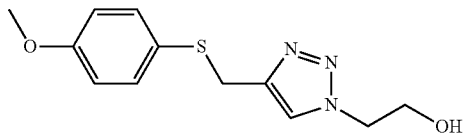 [SMILES: COc1ccc(SCc2cn(CCO)nn2)cc1]

The method of Example 1 was followed starting from 1-(4-methoxyphenylthio)-2-propyne (2.00 mmol, 384 mg) and 2-azidoethanol (2.00 mmol, 174 mg). Yield: 520 mg (98%). Yellowish oil. $^1$H NMR (400 MHz, $CDCl_3$) δ 7.40 (s, 1H), 7.29 (d, J=8.3 Hz, 2H), 6.80 (d, J=8.2 Hz, 2H), 4.40 (s, 2H), 4.09 (s, 2H), 3.99 (s, 2H), 3.77 (s, 3H), 3.18 (s, 1H). $^{13}$C NMR (101 MHz, $CDCl_3$): δ 159.5, 144.9, 133.9, 125.4, 123.5, 114.8, 61.1, 55.5, 52.9, 30.9. HRMS (ESI+, m/z) for $C_{12}H_{15}N_3O_2S$, calculated: 266.0963; detected: 266.0965.

Example 11: 1-carboxymethyl-4-[4-(methoxy)phenylthiomethyl]-1H-1,2,3-triazole

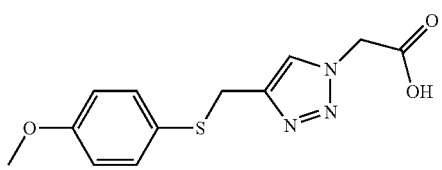 [SMILES: COc1ccc(SCc2cn(CC(=O)O)nn2)cc1]

Lithium hydroxide monohydrate (2.00 mmol, 84 mg) was added to a solution of 1-methoxycarbonylmethyl-4-[4-(methoxy)phenylthiomethyl]-1H-1,2,3-triazole (1.00 mmol, 305 mg, Example 1) in THF/$H_2O$ (1:1, 8 mL) and the resulting mixture was stirred at room temperature for one hour. The organic solvent was evaporated, the resulting aqueous mixture was acidified with 1M HCl, and the solution was extracted with EtOAc (2×10 mL). The pooled organic phases were dried ($MgSO_4$) and the solvent was evaporated at reduced pressure. Yield: 158 mg (54%). White solid. MP: 163-170° C. IR ($cm^{-1}$): 2923, 2848 (C—H), 1730 (C=O), 1223, 1188 (triazole). $^1$H NMR (500 MHz, $CD_3OD$): 7.66 (s, 1H), 7.28 (d, J=8.8 Hz, 2H), 6.84 (d, J=8.8 Hz, 2H), 5.19 (s, 2H), 4.07 (s, 2H), 3.76 (s, 3H). $^{13}$C NMR (125 MHz, $CD_3OD$): δ 169.7, 161.1, 146.3, 135.6, 126.3, 115.7, 55.8, 51.6, 31.5. HRMS (ESI+, m/z) for $C_{12}H_{14}N_3O_3S$, calculated: 280.0756; detected: 280.0760.

Example 12: 1-carboxymethyl-4-[3-(methoxy)phenylthiomethyl]-1H-1,2,3-triazole

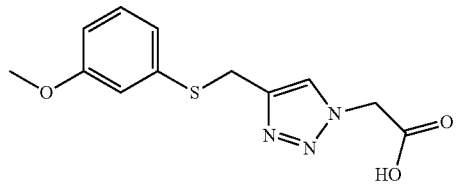 [SMILES: COc1cccc(SCc2cn(CC(=O)O)nn2)c1]

The method of Example 11 was followed starting from 1-methoxycarbonylmethyl-4-[3-(methoxy)phenylthiomethyl]-1H-1,2,3-triazole (1.00 mmol, 305 mg, example 2). Yield: 274 mg (94%). White solid. MP: 115-119° C. IR ($cm^{-1}$): 2999, 2971 (C—H), 1707 (C=O), 1229 (triazole). $^1$H NMR (500 MHz, $CD_3OD$): δ 7.80 (s, 1H), 7.18 (t, J=8.0 Hz, 1H), 6.96-6.86 (m, 2H), 6.76 (dd, J=8.3, 1.8 Hz, 1H), 5.19 (s, 2H), 4.23 (s, 2H), 3.75 (s, 3H). $^{13}$C NMR (125 MHz, $CD_3OD$): δ 169.7, 161.4, 146.1, 138.0, 130.9, 125.9, 123.1, 116.1, 113.6, 55.7, 51.7, 29.3. HRMS (ESI+, m/z) for $C_{12}H_{14}N_3O_3S$, calculated: 280.0756; detected: 280.0753.

Example 13: (S)-1-(1-carboxy-2-phenylethyl)-4-[3-(methoxy)phenylthiomethyl]-1H-1,2,3-triazole

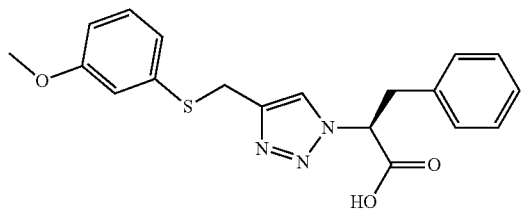 [SMILES: COc1cccc(SCc2cn([C@@H](Cc3ccccc3)C(=O)O)nn2)c1]

The method of Example 11 was followed starting from (S)-1-(1-methoxycarbonyl-2-phenylethyl)-4-[3-(methoxy)phenylthiomethyl]-1H-1,2,3-triazole (1.00 mmol, 383 mg, example 3). Yield: 318 mg (86%). White solid. MP: 79-83° C. $[\alpha]_D^{24}=-23.3°$ (c. 1.12 g/100 mL, $CH_2Cl_2$). IR ($cm^{-1}$): 2931 (C—H), 1727 (C=O), 1246, 1229 (triazole). $^1$H NMR (500 MHz, $CD_3OD$): δ 7.77 (s, 1H), 7.20-6.71 (m, 9H), 5.56 (dd, J=10.8, 4.6 Hz, 1H), 4.15 (s, 2H), 3.73 (s, 3H), 3.56 (dd, J=14.3, 4.5 Hz, 1H), 3.40 (dd, J=14.3, 10.9 Hz, 1H). $^{13}$C NMR (125 MHz, $CD_3OD$): δ 171.1, 161.4, 145.9, 137.9, 137.2, 130.8, 129.9, 128.1, 124.8, 122.9, 115.9, 113.5, 65.8, 55.7. 38.9, 29.0. HRMS (ESI+, m/z) for $C_{20}H_{22}N_3O_3S$, calculated: 384.1382; detected: 384.1392.

Example 14: (R)-1-(1-carboxy-2-phenylethyl)-4-[3-(methoxy)phenylthiomethyl]-1H-1,2,3-triazole

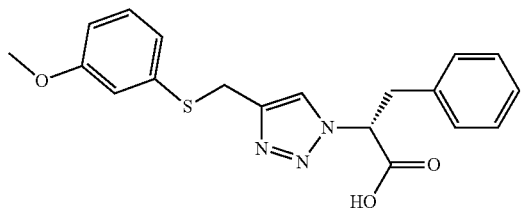 [SMILES: COc1cccc(SCc2cn([C@H](Cc3ccccc3)C(=O)O)nn2)c1]

The method of Example 11 was followed starting from (R)-1-(1-methoxycarbonyl-2-phenylethyl)-4-[3-(methoxy)phenylthiomethyl]-1H-1,2,3-triazole (1.00 mmol, 383 mg, example 4). Yield: 280 mg (76%). White solid. MP: 78-86° C. HRMS (ESI+, m/z) for $C_{20}H_{22}N_3O_3S$, calculated: 384.1382; detected: 384.1382. $[\alpha]_D^{24}$=+16.5° (c. 0.98 g/100 mL, $CH_2Cl_2$). The NMR data was identical to that of Example 13.

Example 15: (S)-1-(1-carboxy-3-methylbutyl)-4-[3-(methoxy)phenylthiomethyl]-1H-1,2,3-triazole

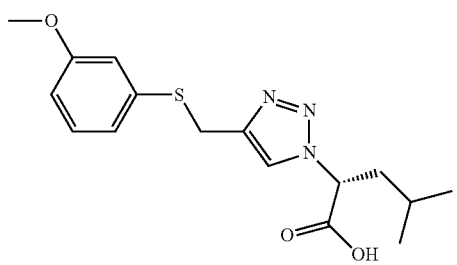 [SMILES: COc1cccc(SCc2cn([C@H](CC(C)C)C(=O)O)nn2)c1]

The method of Example 11 was followed starting from (S)-1-(1-methoxycarbonyl-3-methyl-butyl)-4-[3-(methoxy)phenylthiomethyl]-1H-1,2,3-triazole (1.00 mmol, 349 mg, example 5). Yield: 265 mg (76%). White solid. MP: 96-105° C. $[\alpha]_D^{25.6}$=+9.3° (c. 1.11 g/100 mL, $CH_2Cl_2$). $^1$H NMR (500 MHz, $CDCl_3$): δ 11.88 (s, 1H), 7.54 (s, 1H), 7.12 (t, J=7.9 Hz, 1H), 6.92-6.77 (m, 2H), 6.70 (dd, J=8.1, 1.7 Hz, 1H), 5.38 (dd, J=10.7, 5.0 Hz, 1H), 4.23 (dd, J=40.8, 14.9 Hz, 2H), 3.70 (s, 3H), 2.03-1.86 (m, 2H), 1.17 (dt, J=19.8, 6.5 Hz, 1H), 0.88 (d, J=6.5 Hz, 3H), 0.82 (d, J=6.5 Hz, 3H). $^{13}$C NMR (125 MHz, $CDCl_3$): δ 171.2, 159.8, 144.7, 135.9, 129.8, 122.6, 122.4, 115.6, 112.9, 61.8, 55.3, 41.2, 28.5, 24.7, 22.6, 21.1.

Example 16: (R)-1-(1-carboxy-3-methylbutyl)-4-[3-(methoxy)phenylthiomethyl]-1H-1,2,3-triazole

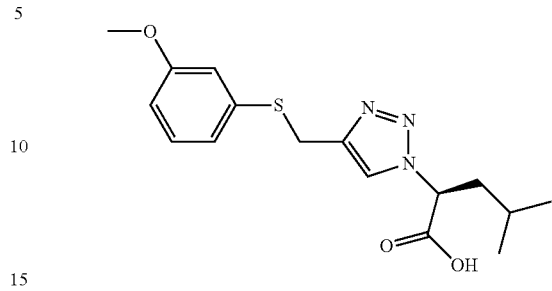

The method of Example 11 was followed starting from (R)-1-(1-methoxycarbonyl-3-methyl-butyl)-4-[3-(methoxy)phenylthiomethyl]-1H-1,2,3-triazole (1.00 mmol, 349 mg, example 6). Yield: 301 mg (86%). White solid. MP: 97-104° C. $[\alpha]_D^{25.4}$=−12.1° (c. 0.95 g/100 mL, $CH_2Cl_2$). The NMR data was identical to that of Example 15.

Example 17: (S)-1-(1-carboxy-2-methylpropyl)-4-[3-(methoxy)phenylthiomethyl]-1H-1,2,3-triazole

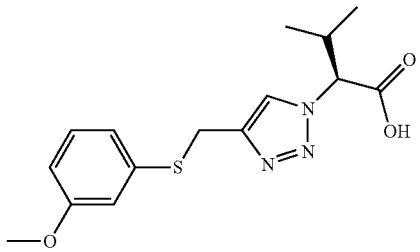 [SMILES: COc1cccc(SCc2cn([C@H](C(=O)O)C(C)C)nn2)c1]

The method of Example 11 was followed starting from (S)-1-(1-methoxycarbonyl-2-methyl-propyl)-4-[3-(methoxy)phenylthiomethyl]-1H-1,2,3-triazole (1.00 mmol, 335 mg, example 7). Yield: 279 mg (87%). White solid. MP: 115-121° C. $[\alpha]_D^{25.6}$=+4.5° (c. 1.06 g/100 mL, $CH_2Cl_2$). $^1$H NMR (500 MHz, $CDCl_3$): δ 11.53 (s, 1H), 7.68 (s, 1H), 7.12 (t, J=7.8 Hz, 1H), 6.87 (d, J=7.4 Hz, 1H), 6.84 (s, 1H), 6.70 (d, J=6.8 Hz, 1H), 5.13 (d, J=7.6 Hz, 1H), 4.23 (dd, J=43.5, 14.5 Hz, 2H), 3.71 (s, 3H), 2.44 (d, J=6.4 Hz, 1H), 0.96 (d, J=6.4 Hz, 3H), 0.75 (d, J=6.4 Hz, 3H). $^{13}$C NMR (125 MHz, $CDCl_3$): δ 170.7, 159.9, 144.6, 136.1, 129.9, 122.9, 122.8, 115.8, 113.0, 69.3, 55.4, 32.2, 28.7, 19.2, 18.3.

Example 18: (R)-1-(1-carboxy-2-methylpropyl)-4-[3-(methoxy)phenylthiomethyl]-1H-1,2,3-triazole

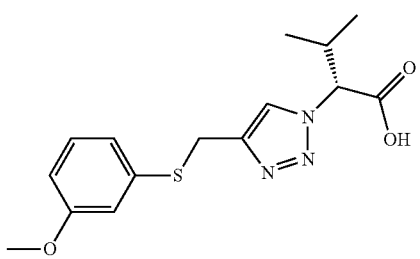 [SMILES: COc1cccc(SCc2cn([C@@H](C(=O)O)C(C)C)nn2)c1]

The method of Example 11 was followed starting from (R)-1-(1-methoxycarbonyl-2-methyl-propyl)-4-[3-(methoxy)phenylthiomethyl]-1H-1,2,3-triazole (1.00 mmol, 335 mg, example 8). Yield: 290 mg (90%). White solid. MP: 114-123° C. $[\alpha]_D^{25.6}=-6.7°$ (c. 1.01 g/100 mL, CH$_2$Cl$_2$). The NMR data was identical to that of Example 17.

Example 19: 1-(1-carboxy-1-methylethyl)-4-[3-(methoxy)phenylthiomethyl]-1H-1,2,3-triazole

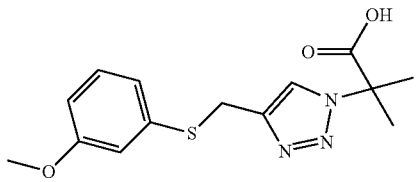 [SMILES: COc1cccc(SCc2cn(C(C)(C)C(=O)O)nn2)c1]

The method of Example 11 was followed starting from 4-[3-(methoxy)phenylthiomethyl]-1-(1-methyl-1-methoxycarbonylethyl)-1H-1,2,3-triazole (0.8 mmol, 258 mg, example 9). Yield: 246 mg (100%). Yellowish solid. MP: 109-121° C. $^1$H NMR (400 MHz, CD$_3$OD): δ 7.77 (s, 1H), 7.09 (t, J=8.0 Hz, 1H), 6.82 (d, J=8.0 Hz, 1H), 6.79 (s, 1H), 6.67 (d, J=8.3 Hz, 1H), 4.12 (s, 2H), 3.65 (s, 3H), 1.78 (s, 6H). $^{13}$C NMR (101 MHz, CD$_3$OD) δ 174.2, 161.3, 145.3, 137.9, 130.8, 123.4, 116.5, 113.7, 65.9, 55.7, 29.5, 25.9.

Example 20: 1-[2-(N,N-dimethylamino)ethyl]-4-[4-(methoxy)phenylthiomethyl]-1H-1,2,3-triazole

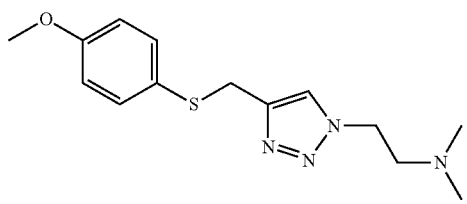

Triethylamine (8.80 mmol, 1.22 mL) and mesyl chloride (4.39 mmol, 0.34 mL) were successively added to a solution of 1-(2-hydroxyethyl)-4-[4-(methoxy)phenylthiomethyl]-1H-1,2,3-triazole (2.92 mmol, 776 mg, example 10) in anhydrous THF (16 mL) cooled at 0° C. under a nitrogen atmosphere. The reaction mixture was stirred at room temperature overnight. Dimethylamine hydrochloride (8.00 mmol, 652 mg), triethylamine (8.80 mmol, 1.22 mL), NaI (0.13 mmol, 20 mg) and an additional amount of anhydrous THF (8 mL) were then added and the mixture was stirred at 50° C. overnight. Upon completion of the reaction, the solvents were evaporated at reduced pressure, the resulting residue was dissolved in EtOAc (20 mL) and successively washed with saturated NaHCO$_3$ aqueous solution (30 mL) and brine (10 mL). The organic layer was dried (MgSO$_4$) and vacuum-evaporated to dryness. Yield: 572 mg (84%). White solid. MP: 35-40° C. IR (cm$^{-1}$): 2943 (N—H), 2860, 2771 (C—H), 1242 (triazole). $^1H$ NMR (400 MHz, CDCl$_3$) δ 7.41 (s, 1H), 7.30 (d, J=7.6 Hz, 2H), 6.81 (d, J=7.8 Hz, 2H), 4.37 (s, 2H), 4.11 (s, 2H), 3.77 (s, 3H), 2.71 (s, 2H), 2.25 (s, 6H). $^{13}$C NMR (101 MHz, CDCl$_3$): 159.2, 144.8, 133.7, 125.5, 122.6, 114.5, 58.6, 55.3, 48.0, 45.3, 30.9. HRMS (ESI+, m/z) for C$_{14}$H$_{21}$N$_4$OS, calculated: 293.1436; detected: 293.1440.

Example 21: 1-methoxycarbonylmethyl-4-(phenylsulfinylmethyl)-1H-1,2,3-triazole

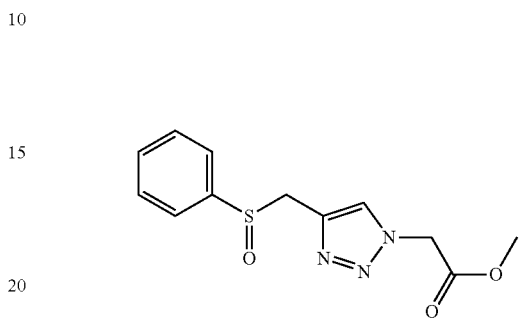

The method of Example 1 was followed starting from phenylthio-2-propyne (2.00 mmol, 268 mg) and methyl azidoacetate (2.00 mmol, 230 mg). Yield: 342 mg (65%). White solid. MP: 70-74° C. IR (cm$^{-1}$): 2953, 2837 (C—H), 1749 (C=O), 1220, 1180 (triazole). $^1$H NMR (400 MHz, CDCl$_3$): δ 7.49 (s, 1H), 7.34 (d, J=7.6 Hz, 2H), 7.31-7.22 (m, 2H), 7.20 (m, 1H), 5.11 (s, 2H), 4.27 (s, 2H), 3.78 (s, 3H). $^{13}$C NMR (101 MHz, CDCl$_3$): δ 166.5, 144.6, 135.1, 129.1, 128.6, 126.1, 123.5, 52.6, 50.3, 28.3. m-chloroperbenzoic acid (1.00 mmol, 172 mg) was added to the resulting solution of 1-(methoxycarbonylmethyl)-4-(phenylthiomethyl)-1H-1,2,3-triazole (1.00 mmol, 263 mg) in anhydrous chloroform (30 mL) at 0° C. and the mixture was stirred at the same temperature for 30 minutes. The mixture was evaporated and the residue was purified by column chromatography (silica gel; 5:95 MeOH/CH$_2$Cl$_2$). Colorless oil. Yield: 161 mg (58%). $^1$H NMR (500 MHz, CDCl$_3$): δ 7.72 (s, 1H), 7.49 (s, 5H), 5.24-5.10 (dd, J=5.13 Hz, 2H), 4.29-4.15 (dd, J=4.28 Hz, 2H), 3.82 (s, 3H).

Example 22: 1-carboxymethyl-4-[3-(methoxy)phenylsulfonylmethyl]-1H-1,2,3-triazole

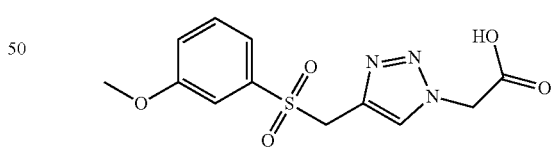

m-chloroperbenzoic acid (2.50 mmol, 437 mg) is added to a solution of 1-(carboxymethyl)-4-[3-(methoxy)phenylthiomethyl]-1H-1,2,3-triazole (1.00 mmol, 279 mg, Example 12) in a 1:1 anhydrous mixture of chloroform/acetonitrile (3 mL) at 0° C. and the mixture is stirred at room temperature overnight. The mixture is evaporated and the residue is purified by column chromatography (silica gel; 5:95 MeOH/CH$_2$Cl$_2$). Yield: 203 mg (65%). White solid. MP: 106-115° C. $^1$H NMR (500 MHz, CDCl$_3$): 7.91 (s, 1H), 7.50-7.29 (Ar, 4H), 4.99 (s, 2H), 4.71 (s, 2H), 3.84 (s, 3H). HRMS (ESI+, m/z) for C$_{12}$H$_{14}$N$_3$O$_5$S, calculated: 312.0654; detected: 312.0662.

Example 23: 1-carboxymethyl-4-[3-(chloro)phenyl-thiomethyl]-1H-1,2,3-triazole

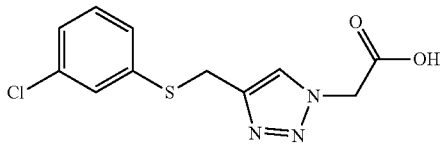 [SMILES: O=C(O)Cn1cc(CSc2cccc(Cl)c2)nn1]

A solution of bromoacetic acid (10 mmol, 1.38 g) and sodium azide (40 mmol, 2.60 g) in water (4 mL) was stirred at room temperature overnight. The solution was then neutralized with 3M NaOH and acetonitrile (15 mL), 1-(3-chlorophenylthio)-2-propyne (8 mmol, 1.45 g), sodium acetate (30 mmol, 2.46 g) and copper(I) acetate (2 mmol, 242 mg) were successively added. The resulting mixture was stirred at 45° C. for 6 hours, the solvent was evaporated, acidified with 1M HCl and extracted with EtOAc (3×20 mL). The pooled organic phases were dried (MgSO$_4$) and the solvent was evaporated at reduced pressure. Yield: 1.49 g (66%). White solid. MP: 146-148° C. IR (cm$^{-1}$): 2928, 2850 (C—H), 1731 (C=O), 1224, 1184 (triazole). $^1$H NMR (500 MHz, CD$_3$OD): 7.86 (s, 1H), 7.39 (s, 1H), 7.28-7.21 (m, 3H), 5.22 (s, 2H), 4.29 (s, 2H). $^{13}$C NMR (125 MHz, CD$_3$OD): δ 168.5, 144.1, 137.9, 134.4, 130.0, 128.8, 127.6, 126.3, 124.6, 50.4, 27.7. HRMS (ESI+, m/z) for C$_{11}$H$_{10}$ClN$_3$O$_2$S, calculated: 283.0182; detected: 283.0190.

Example 24: In Vitro Toxicity Biological Assays in Human Cells

These assays were carried out in human control myotubes LHCN-M2 after 14 days in differentiation medium. To determine the toxicity of the different analyzed compounds, particularly AHK1 and AHK2 according to the invention, these compounds were added to the culture medium for 24 hours at 37° C. at different concentrations (0-2 mM). For comparison purposes, the same assay was performed by adding reference compound S-107. Cell viability was determined by means of Cytotox 96 (Promega) colorimetric assay following instructions in the manual.

The results are shown in FIG. 1 in which it can be seen that the compounds according to the invention do not show in vitro acute toxicity against human myotubes at concentrations between 10 nM and 2 mM. The behavior of compounds AHK1 and AHK2 after 24 hours of incubation is in contrast with the 100% cellular toxicity found for reference compound S-107 at a concentration of 1 mM under identical conditions. This result demonstrates that the compounds according to the invention have a lower toxicity than S-107, suggesting that AHK compounds may be better candidates for the therapeutic treatment of disorders involving abnormal calcium homeostasis in humans.

Example 25. In Vitro Assays for Determining Intracellular Calcium Levels in Mouse Muscle Fibers Fibers isolated from mouse flexor digitorum brevis muscle were cultured overnight in the presence or absence of compounds AHK1 and AHK2 at a concentration of 150 nM. Baseline intracellular calcium levels were evaluated by means of incubating the fibers with Fura 2-AM ratiometric fluorochrome (4 μM) and pluronic acid (0.02%) for 30 minutes at 37° C., in the culture medium. The fibers were viewed with a high-resolution digital camera and intracellular [Ca$^{2+}$] was estimated by means of a 340 nm/380 nm excitation ratio.

Figure 2:
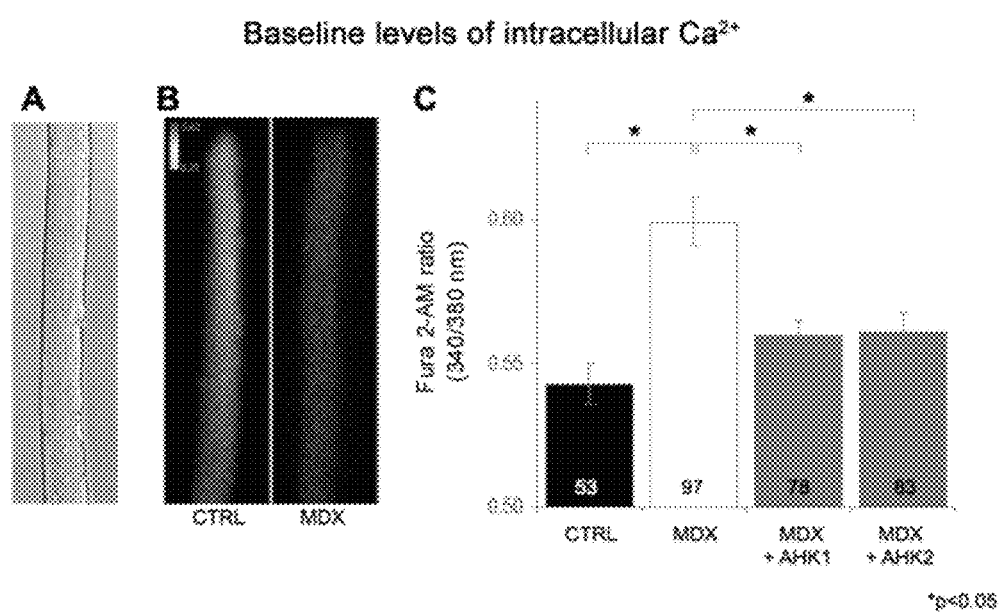
FIG. 2 shows the in vitro effect of compounds AHK1 and AHK2 on intracellular calcium levels in mouse muscle fibers at rest:
A) Image of the fiber isolated from the flexor digitorum brevis muscle showing the characteristic striation pattern. B) Representative images of fibers [control fibers (CTRL) and dystrophic fibers (MDX)] loaded with fura-2AM after performing background correction required for measuring intracellular calcium levels. C) Histogram showing baseline intracellular calcium levels in different groups of fibers. The number of analyzed fibers (n) is shown in the histogram (Kruskal-Wallis and U Mann-Whitney, *p<0.05).

FIG. 2 shows the in vitro effect of compounds AHK1 and AHK2 on at rest intracellular calcium levels in the mentioned mouse muscle fibers. How the untreated dystrophic fibers (MDX) showed a significant increase in calcium levels in comparison with control fibers (CTRL) can be seen. The overnight treatment of MDX fibers with AHK1 and AHK2 brought intracellular calcium levels back to the control levels, which demonstrates the capacity to revert the increase in intracellular calcium observed in muscle fibers. In view of these results, it is postulated that the compounds according to the invention carry out this reversion through a mechanism involving RyR channel modulation.

Example 26. In Vitro Assays on RyR1-Calstabin 1 Interaction

This assay was carried out in human control myotubes LHCN-M2 after 9 days in differentiation medium. Said myotubes were pre-treated for 12 hours with compounds AHK1 and AHK2 at a concentration of 150 nM. After treatment, the myotubes were subjected to peroxynitrite-induced nitro-oxidative stress by means of the addition of SIN1 (5 mM) for 30 minutes.

RyR1-calstabin colocalization was analyzed by means of the in situ proximity ligation technique (in situ PLA) for which Sigma's Duolink II Network Fluorescence Kit and RyR1- and calstabin 1-specific antibodies were used. This technique allows detecting the exact location of two antigens located at a distance less than 40 nm from one another. To determine RyR1-calstabin-1 colocalization, 3 photographs were quantified for each condition with about 9 myotubes per field, using Image J computer software (http://rsb.info.nih.gov/ij/download.html). The colocalization area in each image was normalized to the myosin expression area, which was determined by means of immunofluorescence with a fluorescein-conjugated specific antibody.

Figure 3:
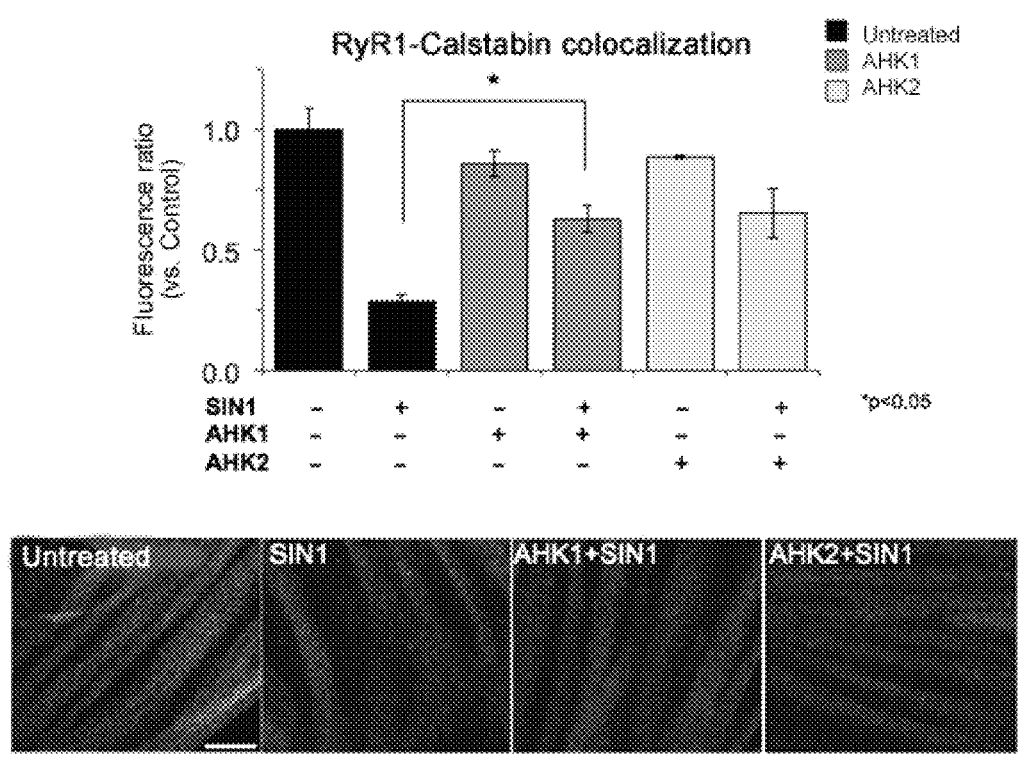
FIG. 3 shows the in vitro effect of compounds AHK1 and AHK2 on the RyR1-calstabin1 interaction in healthy human myotubes cultures exposed to peroxynitrite stress.

As shown in FIG. 3, compounds AHK1 and AHK2 according to the invention have the capacity to partially recover from a decrease in RyR1-calstabin1 interaction in healthy human myotube cultures after being subjected to nitro-oxidative stress. Analyzing RyR1-Calst1 interaction by means of the PLA technique demonstrated that in the presence of SIN1 dissociation of the RyR1-Calst1 complex occurs and that said dissociation can be partially prevented by means of pretreatment with compounds AHK1 and AHK2. The top panel of FIG. 3 shows the quantification of the PLA images with Image J, whereas the bottom panel shows representative images of PLA of each condition, where the points represent the RyR1-Calst1 interaction (50 μm calibration bar). Therefore, the assayed compounds according to the invention not only improve the functionality of Duchenne- or Becker-type dystrophic myotubes, but also minimize the degenerative effects of nitro-oxidative stress on healthy human myotubes through an increase in RyR1-calstabin1 interaction affinity.

According to these results, the compounds of the invention can be useful as therapeutic agents against diseases caused by a decrease in RyR1-calstabin1 affinity under nitro-oxidative stress conditions.

Example 27. In Vivo Biological Assays in Mice

Figure 4:
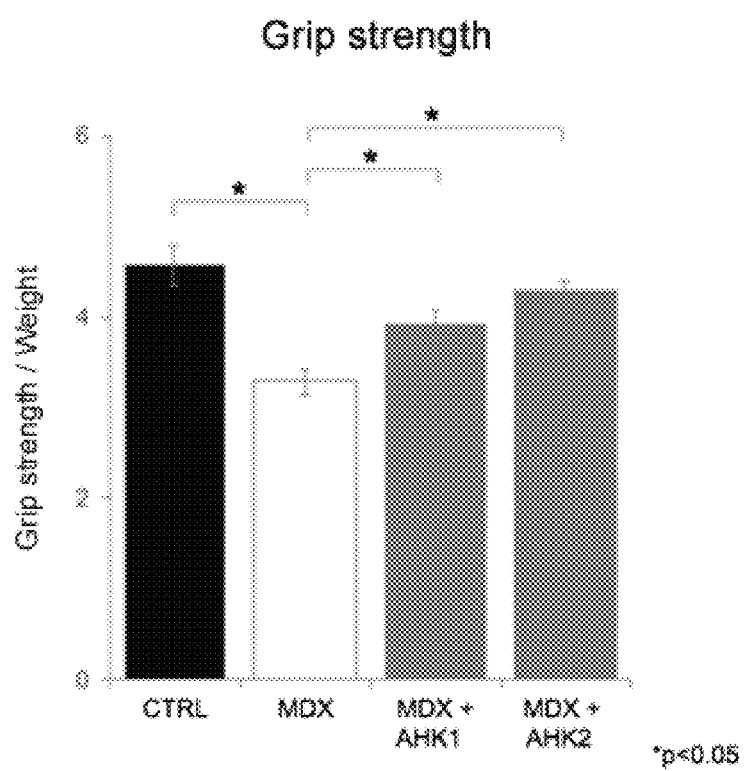
FIG. 4 shows the effect on the grip strength of dystrophic mdx mice treated with compounds AHK1 and AHK2. *p<0.05; n=10 control mice (CTRL); n=11 untreated mdx mice (MDX); n=10 mdx mice treated with AHK1 (MDX+AHK1); and n=6 mdx mice treated with AHK2 (MDX+AHK2).

One-month old male dystrophic mdx mice supplied by Jackson Laboratory (https://www.jax.org/strain/001801)

were used. The biological assays for measuring the effect of the Ahulken (AHK) compounds on muscle function were performed with one-month old mice, whereas the in vivo assays for determining the effect on the heart and CNS were performed with four-month old mice. The one-month old mice were treated with compound AHK1 or compound AHK2 for 5 weeks, where said compounds were administered in drinking water at a concentration of 0.25 mg/mL. The muscle strength of the front paws was measured every week using a grip strength meter and the obtained value was normalized by the body weight of the animal. To that end, the indications described in the TREAT-NMD Neuromuscular Network protocol (http://www.treat-nmd.eu/downloads/file/sops/dmd/MDX/DMD_M.2.2.001.pdf) were followed. The dystrophic mice showed a significant decrease in grip strength. However, after 2 weeks of treatment the strength increased significantly in mdx mice treated with AHK1 or AHK2 compared to untreated littermates. After 5 weeks of treatment, the muscle strength increased significantly by 20% (FIG. 4).

This data suggests that the compounds according to the invention may be effective for treating patients with muscular dystrophies by means of improving muscle function or preventing muscle weakness.

Figure 5:
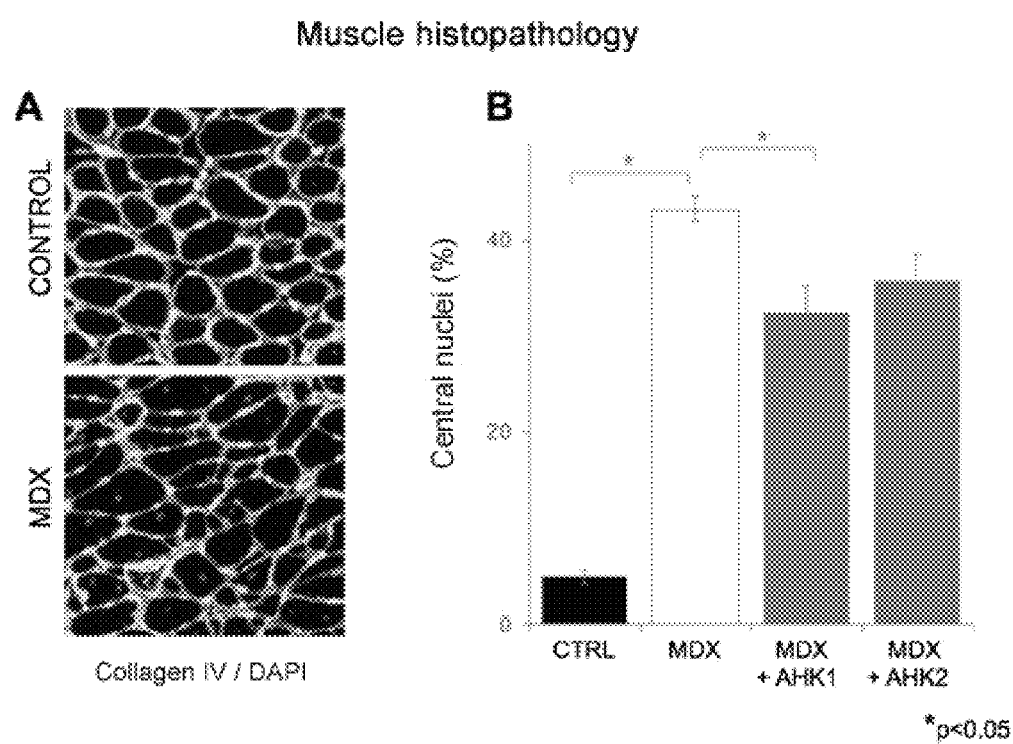
FIG. 5 shows the in vivo effect of compounds AHK1 and AHK2 on muscle degeneration/regeneration in dystrophic mdx mice:
A) Representative cryostat sections of control and dystrophic mice diaphragms in which collagen IV labeled with a fluorescent antibody and nuclei labeled with 4',6-diamidino-2-phenylindole (DAPI) are observed.
B) Number of central nuclei obtained in sections of control mice (CTRL), dystrophic mice (MDX) and dystrophic mice treated with AHK1 (MDX+AHK1) and AHK2 (MDX+AHK2). *p<0.05; n=3 CTRL; n=7 MDX ND; n=7 MDX+AHK1 and n=4 MDX+AHK2).
Figure 6:
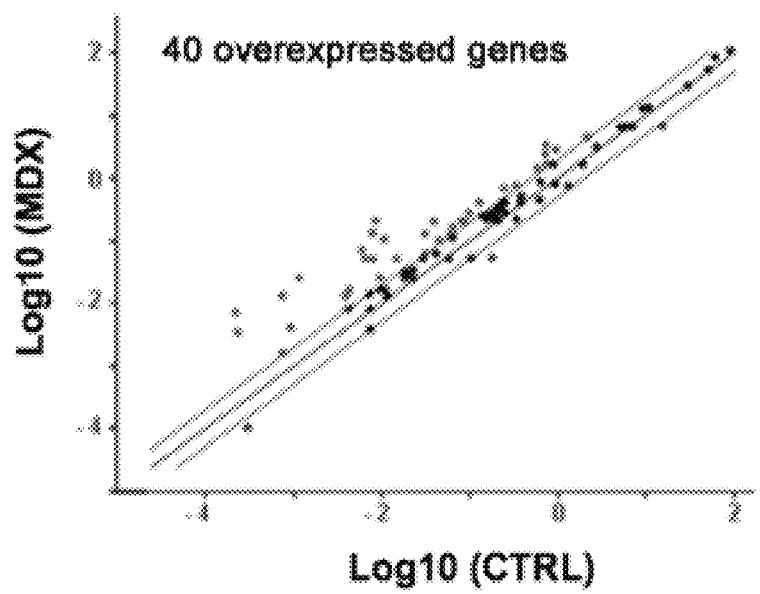
FIG. 6 shows the effect of treatment with AHK1 on the gene expression pattern of the tibialis anterior muscle of mdx mice.
Figure 6:
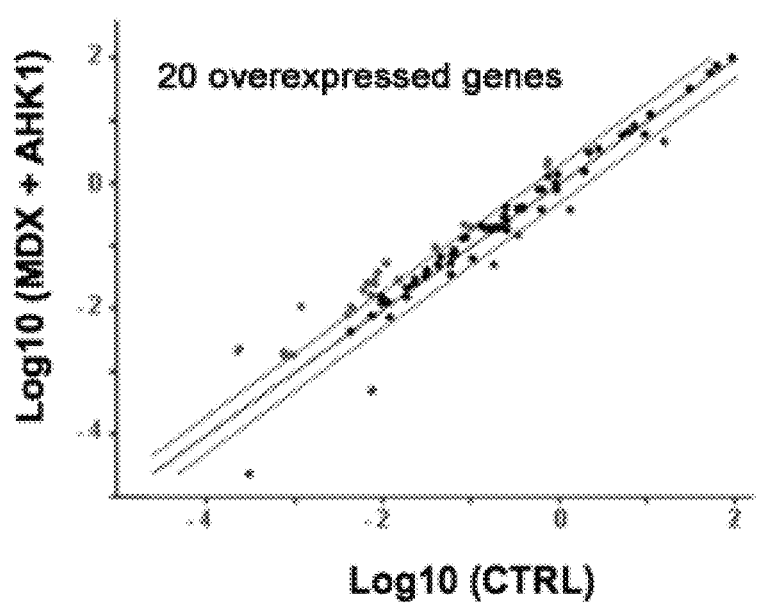

After concluding the 5-week treatment, the tibialis anterior muscle was obtained and processed for subsequent biochemical and immunohistological analysis to determine the degree of muscle damage. Cell-death derived regeneration was determined in muscle cryosections by means of quantifying the percentage of central nuclei using standard immunofluorescence techniques for detecting collagen IV and cell nuclei. FIG. 5 shows representative cryostat sections of control and dystrophic mice diaphragms labeled in order to view collagen IV and DAPI in order to view the nuclei. The 5-week treatment of mdx mice with AHK1 and AHK2 significantly reduced the percentage of central nuclei, which clearly shows the capacity of said compounds to reduce histopathological markers of muscular dystrophy after 5 weeks of treatment. These results suggest that the compounds according to the invention are effective in vivo and reach skeletal muscle.

In turn, the biochemical analysis of the tibialis anterior muscle was performed by means of RNA extraction and expression pattern analysis in control mice, mdx mice and mice subjected to different treatments. To that end, the human skeletal muscle, myogenesis and myopathy RT Profiler PCR Array (PAHS-099Z, QIAGEN) was used, using cDNA mixtures of at least 3 mice per group. The expression profile of 84 genes involved in physiopathological mechanisms of the skeletal muscle was thus analyzed. The experiments were conducted in 7300 Real-Time PCR equipment (Applied Biosystems) and the results obtained were analyzed using QIAGEN online software (http://www.sabiosciences.com/dataanalysis.php).

The treatment of mdx mice with compound AHK1 for 5 weeks leads to the gene expression pattern of mdx mice being partially regained, as shown by means of comparing the gene expression of WT and mdx mice in FIG. 5. There were 40 genes the expression of which was increased in mdx mice with respect to control, and this number dropped to 20 in mice treated with AHK1 (MDX+AHK1). A gene was considered overexpressed when the expression thereof increased by at least 1.75-fold with respect to the control. Table 1 shows the list of genes the expression of which is increased in mdx mice and drops to control values, which decreases partially or does not change with AHK1 treatment.

TABLE 1

| Symbol | Unigene | RefSeq | MDX | MDX + AHK1 |
|---|---|---|---|---|
| Overexpressed genes the expression of which is normalized with AHK1 | | | | |
| Akt1 | Mm.6645 | NM_009652 | 2.63 | 1.42 |
| Bcl2 | Mm.257460 | NM_009741 | 1.94 | 1.05 |
| Cast | Mm.441995 | NM_009817 | 1.86 | 1.49 |
| Cav3 | Mm.3924 | NM_007617 | 3.28 | 1.68 |
| Cryab | Mm.178 | NM_009964 | 3.08 | 1.50 |
| Ctnnb1 | Mm.291928 | NM_007614 | 1.79 | 1.27 |
| Dag1 | Mm.491797 | NM_010017 | 2.27 | 1.23 |
| Des | Mm.6712 | NM_010043 | 2.14 | 1.53 |
| Dysf | Mm.220982 | NM_021469 | 2.15 | 1.28 |
| Foxo3 | Mm.391700 | NM_019740 | 1.76 | 1.14 |
| Igfbp3 | Mm.29254 | NM_008343 | 1.77 | 1.34 |
| Igfbp5 | Mm.405761 | NM_010518 | 2.52 | 1.43 |
| Ikbkb | Mm.277886 | NM_010546 | 2.72 | 1.62 |
| Mapk3 | Mm.8385 | NM_011952 | 2.61 | 1.69 |
| Myod1 | Mm.1526 | NM_010866 | 4.27 | 1.28 |
| Nfkb1 | Mm.256765 | NM_008689 | 2.45 | 1.67 |
| Ppargc1b | Mm.415302 | NM_133249 | 1.77 | 1.23 |
| Prkaa1 | Mm.207004 | NM_001013367 | 2.33 | 1.55 |
| Rps6kb1 | Mm.446624 | NM_028259 | 1.77 | 1.25 |
| Utrn | Mm.418026 | NM_011682 | 2.03 | 1.35 |
| Overexpressed genes partially normalized with AHK1 | | | | |
| Casp3 | Mm.34405 | NM_009810 | 10.28 | 5.27 |
| Igf2 | Mm.3862 | NM_010514 | 22.31 | 9.78 |
| Il1b | Mm.222830 | NM_008361 | 17.77 | 2.82 |
| Il6 | Mm.1019 | NM_031168 | 32.72 | 9.76 |
| Lmna | Mm.471227 | NM_019390 | 5.29 | 2.52 |
| Mmp9 | Mm.4406 | NM_013599 | 4.51 | 2.01 |
| Myog | Mm.16528 | NM_031189 | 17.36 | 3.24 |
| Tgfb1 | Mm.248380 | NM_011577 | 6.51 | 3.61 |
| Tnnc1 | Mm.439921 | NM_009393 | 25.00 | 4.53 |
| Tnnt1 | Mm.358643 | NM_011618 | 12.09 | 3.37 |
| Overexpressed genes the expression of which does not change with AHK1 | | | | |
| Bmp4 | Mm.6813 | NM_007554 | 1.93 | 2.08 |
| Capn2 | Mm.19306 | NM_009794 | 2.90 | 1.75 |
| Igf1 | Mm.268521 | NM_010512 | 2.87 | 2.07 |
| Tnf | Mm.1293 | NM_013693 | 15.01 | 10.27 |
| Prkag3 | Mm.453463 | NM_153744 | 2.52 | 2.68 |
| Rhoa | Mm.318359 | NM_016802 | 2.30 | 1.80 |
| Pax3 | Mm.1371 | NM_008781 | 2.16 | 2.48 |
| Pax7 | Mm.218760 | NM_011039 | 3.82 | 2.55 |
| Musk | Mm.16148 | NM_010944 | 3.51 | 2.00 |
| Myf5 | Mm.4984 | NM_008656 | 3.40 | 2.13 |

Specifically, the results clearly show that the compounds according to the invention show the capacity to reduce the number of genes overexpressed in dystrophic mdx muscle by half. Genes that can be modulated by means of AHK compounds include, but are not limited to, Akt1, Bcl2, Casp3, Cast, Cav3, Cryab, Ctnnb1, Dag1, Des, Dysf, Foxo3, Igfbp3, Igfbp5, Ikbkb, Mapk3, Myod1, Nfkb1, Ppargc1b, Prkaa1, Rps6kb1, Utr, Casp3, Igf2, Il1b, Il6, Lmna, Mmp9, Myog, Tgfb1, Tnnc1 and Tnnt1. Within this list, Akt1, Il1b, Mapk3, Mmp9 and Utr are genes related to skeletal muscle loss or atrophy.

Figure 7:
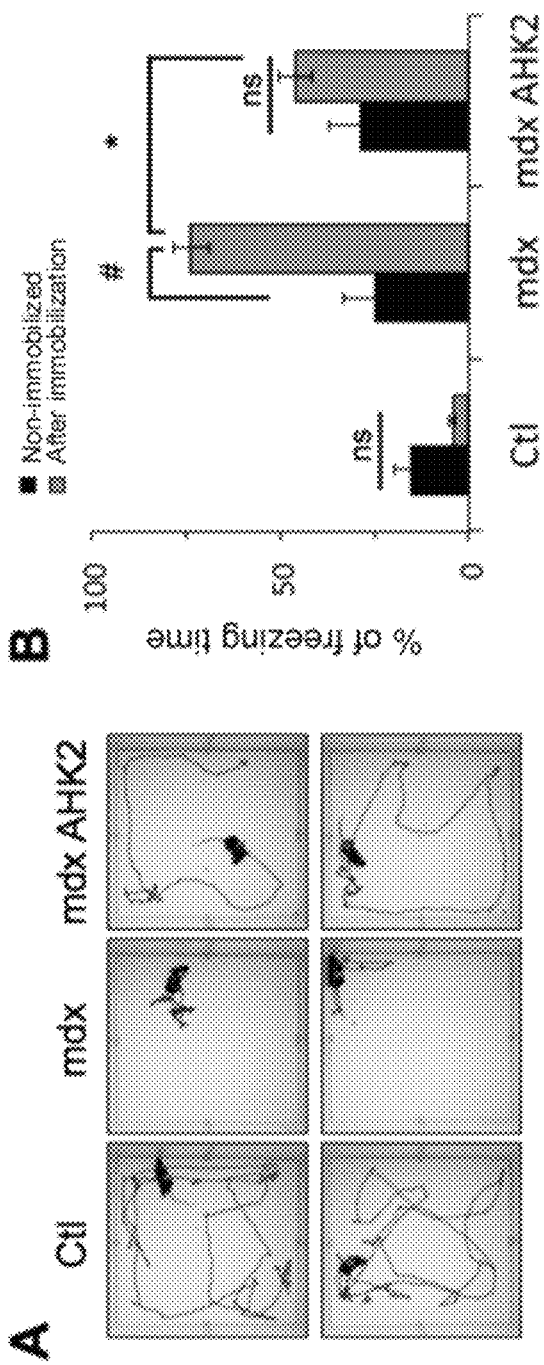
FIG. 7 shows the in vivo effect of compound AHK2 on abnormal CNS functioning in dystrophic mdx mice:
A) 1-minute trajectories of the control mice (Ctl), mdx mice (mdx) and mdx mice treated with AHK2 (mdx AHK2), after a brief 15-second immobilization;
B) exacerbated defense response after acute stress expressed as the percentage of time the mouse performs freezing for the duration of 1 minute. (Gray bars): tonic immobility periods of at least 1 second with 90% immobility sensitivity; (Black bars): percentage of freezing time in non-immobilized animals.
*P<0.05 (unpaired t-test); #p<0.05 (paired t-test); ns, not significant; n≥5 mice per group, error ±SEM bars.

To determine the effect of the compounds according to the invention on the heart and CNS, four-month old mice were treated for 5 weeks with compound AHK2 in drinking water at a concentration of 0.25 mg/mL. The four-month old mdx mice show an exacerbated defense response after acute stress which is independent of motor, cardiac and respiratory deficiencies, and is controlled by central mechanisms (FIG. 7). Acute stress was brought about by means of manual immobilizations for 15 seconds in a posture commonly used for performing intraperitoneal injections. After acute stress, the mice are monitored for 1 minute and the % of freezing time or tonic immobility periods of at least 1 second with 90% immobility sensitivity is calculated. No differences were observed in the freezing of mice not subjected to stress, which indicates that the exacerbated defense response shown by mdx mice is independent of motor deficiencies. A five-week AHK2 treatment significantly improves the exacerbated defense response-related CNS phenotype of mdx mice. These results suggest that the compounds according to the invention are effective in vivo for treating alterations in brain function and they reach the CNS.

Figure 8:
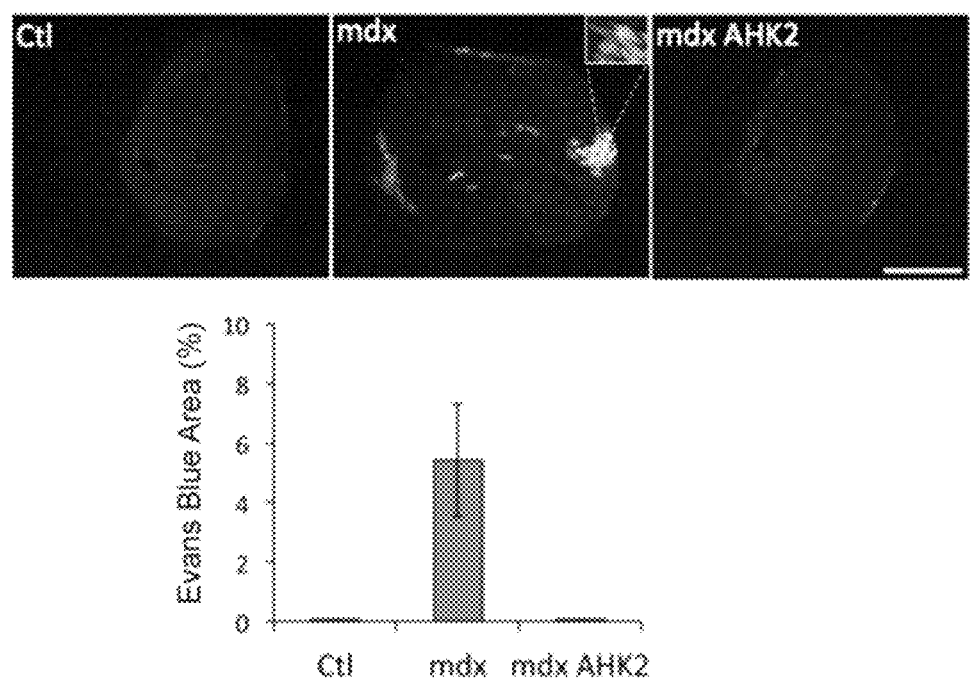
FIG. 8 shows the in vivo effect of compound AHK2 on isoproterenol-induced cardiomyopathy in mdx mice.
Top panel: representative images of heart sections of control mice BL10 (Ctl), mdx mice (mdx) and mdx mice treated with AHK2 (mdx AHK2). Calibration bar, 1 mm. Evans Blue uptake is seen by means of fluorescence microscopy.

The myocardium of the four-month old dystrophic mdx mice is highly susceptible to mechanical stress and the compound isoproterenol induces cardiomyopathy in these mice (FIG. 8). Cardiomyocyte sarcolemma integrity was determined by means of measuring the uptake of Evans Blue dye that accumulates in cardiomyocytes with membrane damage. Evans Blue was administered 24 hours before extracting the hearts at a concentration of 10 mg/ml by means of intraperitoneal injection (10 µl/g of body weight). Damage with isoproterenol was carried out by means of 3 sequential intraperitoneal injections of beta-isoproterenol (350 ng/g of body weight) 18, 20 and 22 hours after administering Evans Blue in order to determine the degree of muscle damage. Cell-death derived regeneration was determined in muscle cryosections by means of quantifying the percentage of central nuclei, using standard immunofluorescence techniques for detecting collagen IV and cell nuclei. FIG. 8 shows representative cryostat sections of the hearts of control mice and dystrophic mice injected with Evans Blue to view the heart damage caused by isoproterenol. The 5-week treatment of mdx mice with AHK2 increases cardiomyocyte sarcolemma integrity of mdx mice and protects the myocardium from isoproterenol-induced damage, which indicates that said compound reaches the heart muscle, is capable of modulating type 2 ryanodine receptor (RyR2) and is effective in vivo for preventing cardiomyopathies.

The invention claimed is:

1. A compound of formula (I):

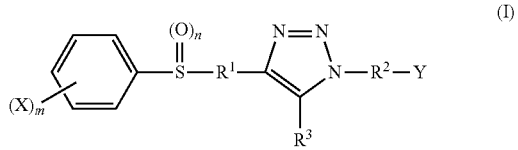

where
$R^1$ is a $C_{1-4}$ alkylene biradical optionally substituted with one or more substituents independently selected from the group consisting of $C_{1-4}$ alkyl, $C_{6-10}$ aryl, F, Cl, CN and $NO_2$;
$R^2$ is a $C_{1-4}$ alkylene biradical optionally substituted with one or two substituents independently selected from the group consisting of methyl, ethyl, propyl, isopropyl, allyl, propargyl, butyl, isobutyl, sec-butyl, tert-butyl, hydroxymethyl, 1-hydroxyethyl, 2-hydroxyethyl, 3-aminopropyl, 4-aminobutyl, 3-guanidylpropyl, 3-indolylmethyl, phenyl, 1-naphthyl, 2-naphthyl, benzyl, 4-hydroxybenzyl, $C_{6-10}$ heteroaryl;
$R^3$ is H;
m is selected from 0, 1, 2 and 4;
n is selected from 0, 1 and 2;
X is independently selected from the group consisting of OH, $O(C_{1-4}$ alkyl), $O(C_{6-10}$ aryl), $OCF_3$, $S(C_{1-4}$ alkyl), $S(C_{6-10}$ aryl), $C_{1-6}$ alkyl, $CF_3$, $NHC(O)(C_{1-4}$ alkyl) and halogen; or two X groups can represent a methylenedioxy, ethylenedioxy or propylenedioxy biradical; and
Y is selected from the group consisting of —$CO_2H$, —$CO_2(C_{1-4}$ alkyl), —$N(C_{1-4}$ alkyl)$_2$, or a pharmaceutically acceptable stereoisomer, salt, solvate or complex thereof, or an isotopically labeled derivative.

2. The compound according to claim 1, wherein $R^1$ is —$CH_2$—.

3. The compound according to claim 1, wherein $R^2$ is a —$CH_2$— or —$CH_2$—$CH_2$— biradical, optionally substituted with one or two substituents independently selected from the group consisting of methyl, isopropyl, isobutyl and benzyl.

4. The compound according to claim 3, wherein $R^2$ is a —$CH_2$— biradical optionally substituted with two methyl substituents or with one substituent selected from the group consisting of isopropyl, isobutyl and benzyl, or wherein $R^2$ is a —$CH_2$—$CH_2$— biradical.

5. The compound according to claim 4, wherein $R^2$ is a —$CH_2$— or —$CH_2$—$CH_2$— biradical.

6. The compound according to claim 1, wherein m 1.

7. The compound according to claim 1, wherein n is 0.

8. The compound according to claim 1, wherein X is $O(C_{1-4}$ alkyl) or halogen.

9. The compound according to claim 8, wherein X is a methoxy group in meta or para position or chlorine.

10. The compound according to claim 1, wherein Y is selected from the group consisting of $CO_2H$, $CO_2Me$, —$NMe_2$, —$NEt_2$ or a pharmaceutically acceptable salt of said groups.

11. The compound according to claim 10, wherein Y is selected from the group consisting of $CO_2H$ and —$NMe_2$.

12. The compound of formula (I) according to claim 1, selected from the group consisting of:

1-carboxymethyl-4-[3-(methoxy)phenylthiomethyl]-1H-1,2,3-triazole,

1-[2-(N,N-dimethylamino)ethyl]-4-[4-(methoxy)phenylthiomethyl]-1H-1,2,3-triazole, 1-carboxymethyl-4-[4-(methoxy)phenylthiomethyl]-1H-1,2,3-triazole, (S)-1-(1-carboxy-2-phenylethyl)-4-[3-(methoxy)phenylthiomethyl]-1H-1,2,3-triazole, (R)-1-(1-carboxy-2-phenylethyl)-4-[3-(methoxy)phenylthiomethyl]-1H-1,2,3-triazole, (S)-1-(1-carboxy-3-methylbutyl)-4-[3-(methoxy)phenylthiomethyl]-1H-1,2,3-triazole, (R)-1-(1-carboxy-3-methylbutyl)-4-[3-(methoxy)phenylthiomethyl]-1H-1,2,3-triazole, (S)-1-(1-carboxy-2-methylpropyl)-4-[3-(methoxy)phenylthiomethyl]-1H-1,2,3-triazole, (R)-1-(1-carboxy-2-methylpropyl)-4-[3-(methoxy)phenylthiomethyl]-1H-1,2,3-triazole, 1-(1-carboxy-1-methylethyl)-4-[3-(methoxy)phenylthiomethyl]-1H-1,2,3-triazole, 1-(2-hydroxyethyl)-4-[4-(methoxy)phenylthiomethyl]-1H-1,2,3-triazole, 1-methoxycarbonylmethyl-4-(phenylsulfinylmethyl)-1H-1,2,3-triazole, and 1-carboxymethyl-4-[3-(methoxy)phenylsulfonylmethyl]-1H-1,2,3-triazole, 1-carboxymethyl-4-[3-(chloro)phenylthiomethyl]-1H-1,2,3-triazole, or a salt thereof.

13. A pharmaceutical composition comprising a compound of formula (I) as defined in claim 1, and one or more pharmaceutically acceptable excipients or vehicles.

14. The pharmaceutical composition according to claim 13 for oral or parenteral administration.

15. A method for the treatment of skeletal muscle disorders and diseases, heart disorders and diseases and nervous system disorders and diseases, which comprises administering a therapeutically effective amount of a compound of formula (I) as defined in claim 1, wherein the disorder is selected from Duchenne muscular dystrophy, Becker muscular dystrophy, or Alzheimer's disease.

16. The method according to claim 15, where the skeletal muscle disorders and disease is Duchenne muscular dystrophy or Becker muscular dystrophy.

17. The method according to claim 15, where the nervous system disorders and diseases is Alzheimer's disease.

18. A method for synthesizing a compound of formula (I) as defined in claim 1, comprising:
  a) reacting an alkyne of formula (II) with an azide of formula (III),

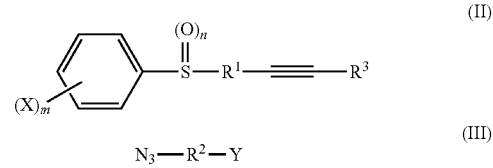

optionally in the presence of a copper catalyst, and optionally in the presence of a base to yield a compound of formula (I), wherein:
  groups $R^1$, $R^2$, $R^3$, m, n and X in the compounds of formulae (II)-(III) are as defined in claim 1, and
  Y is a group as defined in claim 1, optionally protected with a carboxyl protecting group, a hydroxyl protecting group or an amino protecting group;
  b) when n is 0 in the compound of formula (I) obtained in step a), optionally treating said compound of formula (I) with an oxidizing agent to yield a compound of formula (I) wherein n is 1 or 2, $R^1$, $R^2$, $R^3$, m and X are as defined in claim 1, and Y is a group as defined in claim 1, optionally protected with a carboxyl protecting group, a hydroxyl protecting group or an amino protecting group; and
  c) when the compound of formula (I) obtained in step a) or b) has a Y group protected with a protecting group, removing said protecting group to yield a compound of formula (I) wherein $R^1$, $R^2$, $R^3$, m, n, X and Y are as defined in claim 1.

* * * * *